(12) United States Patent
Mark et al.

(10) Patent No.: US 11,759,259 B2
(45) Date of Patent: Sep. 19, 2023

(54) TISSUE REMOVAL DEVICE WITH ADJUSTABLE DELIVERY SLEEVE FOR NEUROSURGICAL AND SPINAL SURGERY APPLICATIONS

(71) Applicant: Nico Corporation, Indianapolis, IN (US)

(72) Inventors: Joseph L. Mark, Indianapolis, IN (US); Brian C. Dougherty, Terre Haute, IN (US)

(73) Assignee: Nico Corporation, Indianapolis, IN (US)

( * ) Notice: Subject to any disclaimer, the term of this patent is extended or adjusted under 35 U.S.C. 154(b) by 1149 days.

(21) Appl. No.: 16/138,984

(22) Filed: Sep. 22, 2018

(65) Prior Publication Data

US 2019/0021754 A1    Jan. 24, 2019

Related U.S. Application Data

(63) Continuation of application No. 13/269,339, filed on Oct. 7, 2011, now Pat. No. 10,080,578, which is a
(Continued)

(51) Int. Cl.
*A61B 18/22* (2006.01)
*A61B 10/02* (2006.01)
(Continued)

(52) U.S. Cl.
CPC .......... *A61B 18/22* (2013.01); *A61B 10/0275* (2013.01); *A61B 17/32002* (2013.01); *A61B 10/0283* (2013.01); *A61B 2010/0208* (2013.01); *A61B 2017/00017* (2013.01); *A61B 2017/00738* (2013.01); *A61B 2017/00977* (2013.01); *A61B 2017/2929* (2013.01); *A61B 2017/320028* (2013.01); *A61B 2017/3445* (2013.01);
(Continued)

(58) Field of Classification Search
CPC ........ A61B 10/0275; A61B 2010/0208; A61B 2017/320028; A61M 1/0039; A61M 1/0064
See application file for complete search history.

(56) References Cited

U.S. PATENT DOCUMENTS 2,044,823 A    6/1936  Whiteside
D161,178 S    12/1950  Waldron
(Continued)

FOREIGN PATENT DOCUMENTS

AU    2011253790 A1    1/2012
EP    0125070 A2    11/1984
(Continued)

OTHER PUBLICATIONS

Publication entitled "Extending Your Arthroscopic Reach", published by Smith&Nephew Dyonics, Inc., Feb. 1992.
(Continued)

*Primary Examiner* — Sean P Dougherty
(74) *Attorney, Agent, or Firm* — Brooks Kushman, P.C.

(57) ABSTRACT

A tissue cutting device is disclosed and described. The device includes a handpiece and an outer cannula in which a reciprocating inner cannula is disposed. A delivery sleeve may be selectively provided that is configured to be disposed about the outer cannula for delivery of a variety of devices.

20 Claims, 19 Drawing Sheets

Related U.S. Application Data continuation-in-part of application No. 12/475,258, filed on May 29, 2009, now Pat. No. 9,216,031, which is a continuation-in-part of application No. 12/435,724, filed on May 5, 2009, now Pat. No. 8,460,327, which is a continuation-in-part of application No. 12/404,407, filed on Mar. 16, 2009, now Pat. No. 8,496,599, which is a continuation-in-part of application No. 12/391,579, filed on Feb. 24, 2009, now Pat. No. 8,702,738, which is a continuation-in-part of application No. 12/389,447, filed on Feb. 20, 2009, now Pat. No. 9,655,639, which is a continuation-in-part of application No. 12/336,054, filed on Dec. 16, 2008, now Pat. No. 8,430,825, and a continuation-in-part of application No. 12/336,086, filed on Dec. 16, 2008, now Pat. No. 8,657,841.

(51) Int. Cl.
| | | |
|---|---|---|
| *A61B 17/32* | (2006.01) | |
| *A61B 17/34* | (2006.01) | |
| *A61B 90/00* | (2016.01) | |
| *A61B 17/00* | (2006.01) | |
| *A61B 17/29* | (2006.01) | |
| *A61M 1/00* | (2006.01) | |

(52) U.S. Cl.
CPC . *A61B 2090/3614* (2016.02); *A61B 2090/392* (2016.02); *A61B 2217/005* (2013.01); *A61B 2217/007* (2013.01); *A61M 1/76* (2021.05); *A61M 1/774* (2021.05)

(56) References Cited

U.S. PATENT DOCUMENTS

| | | | | |
|---|---|---|---|---|
| 3,815,604 | A | 6/1974 | O'Malley et al. | |
| 3,916,903 | A * | 11/1975 | Pozzi | A61M 16/0472 128/207.29 |
| 4,071,029 | A | 1/1978 | Richmond et al. | |
| 4,210,146 | A | 7/1980 | Banko | |
| 4,314,450 | A | 2/1982 | Pelioux-Gervais | |
| 4,493,698 | A | 1/1985 | Wang et al. | |
| 4,650,460 | A | 3/1987 | Roizenblatt | |
| 4,770,654 | A | 9/1988 | Rogers et al. | |
| 4,940,061 | A | 7/1990 | Terwilliger et al. | |
| 5,048,538 | A | 9/1991 | Terwilliger et al. | |
| 5,085,658 | A | 2/1992 | Meyer | |
| 5,098,426 | A | 3/1992 | Sklar et al. | |
| 5,106,364 | A | 4/1992 | Hayafuji et al. | |
| 5,195,541 | A | 3/1993 | Obenchain | |
| 5,250,038 | A * | 10/1993 | Melker | A61M 25/0032 604/167.01 |
| 5,403,276 | A | 4/1995 | Schechter et al. | |
| 5,411,513 | A | 5/1995 | Ireland et al. | |
| 5,415,169 | A | 5/1995 | Siczek et al. | |
| 5,456,689 | A | 10/1995 | Kresch et al. | |
| 5,533,986 | A * | 7/1996 | Mottola | A61M 25/0014 604/264 |
| 5,643,304 | A | 7/1997 | Schechter et al. | |
| 5,647,859 | A * | 7/1997 | Lampropoulos | A61M 25/0014 604/264 |
| 5,669,394 | A | 9/1997 | Bergery et al. | |
| 5,772,627 | A | 6/1998 | Acosta et al. | |
| 5,772,639 | A * | 6/1998 | Lampropoulos | A61M 25/0014 604/264 |
| 5,782,849 | A | 7/1998 | Miller | |
| 5,810,744 | A | 9/1998 | Chu et al. | |
| 5,855,559 | A * | 1/1999 | Van Tassel | A61B 17/00491 600/486 |
| 5,911,701 | A | 6/1999 | Miller et al. | |
| 5,916,231 | A | 6/1999 | Bays | |
| 5,997,560 | A | 12/1999 | Miller | |
| 6,017,354 | A | 1/2000 | Culp et al. | |
| 6,024,751 | A | 2/2000 | Lovato et al. | |
| 6,032,673 | A | 3/2000 | Savage et al. | |
| 6,086,544 | A | 7/2000 | Hibner et al. | |
| 6,152,871 | A | 11/2000 | Foley et al. | |
| 6,162,203 | A * | 12/2000 | Haaga | A61B 10/0275 128/898 |
| 6,179,829 | B1 | 1/2001 | Bisch et al. | |
| 6,245,084 | B1 | 6/2001 | Mark et al. | |
| 6,258,111 | B1 | 7/2001 | Ross et al. | |
| 6,269,888 | B1 | 8/2001 | Schuda et al. | |
| 6,302,873 | B1 * | 10/2001 | Moenning | A61B 17/3417 604/164.09 |
| 6,312,441 | B1 | 11/2001 | Deng | |
| 6,322,549 | B1 | 11/2001 | Eggers et al. | |
| 6,328,730 | B1 | 12/2001 | Harkrider, Jr. | |
| 6,354,104 | B1 | 3/2002 | Feagin | |
| 6,402,701 | B1 | 6/2002 | Kaplan et al. | |
| 6,419,641 | B1 | 7/2002 | Mark et al. | |
| 6,485,436 | B1 * | 11/2002 | Truckai | A61B 10/0275 600/564 |
| 6,491,699 | B1 | 12/2002 | Henderson et al. | |
| 6,592,530 | B1 | 7/2003 | Farhadi | |
| 6,609,020 | B2 | 8/2003 | Gill | |
| D479,455 | S | 9/2003 | Waldron | |
| 6,629,986 | B1 | 10/2003 | Ross et al. | |
| 6,659,998 | B2 | 12/2003 | DeHoogh et al. | |
| 7,019,234 | B1 | 3/2006 | Mezhinsky et al. | |
| 7,226,459 | B2 | 6/2007 | Cesarini et al. | |
| 7,347,829 | B2 | 3/2008 | Mark et al. | |
| 7,350,592 | B2 | 4/2008 | Hahn et al. | |
| 7,481,775 | B2 | 1/2009 | Weikel, Jr. et al. | |
| 7,678,552 | B2 | 3/2010 | Kornblith | |
| 8,109,908 | B1 * | 2/2012 | Kraus | A61M 25/0009 604/164.03 |
| 8,187,229 | B2 | 5/2012 | Weitzner et al. | |
| 9,186,175 | B2 * | 11/2015 | Mark | A61B 1/0607 |
| 9,265,899 | B2 * | 2/2016 | Albrecht | A61M 13/003 |
| 2001/0037114 | A1 | 11/2001 | Dinger et al. | |
| 2002/0103496 | A1 | 8/2002 | Harper et al. | |
| 2003/0045811 | A1 | 3/2003 | Hinchliffe et al. | |
| 2003/0047434 | A1 | 3/2003 | Hanson et al. | |
| 2003/0073980 | A1 | 4/2003 | Finlay et al. | |
| 2003/0208136 | A1 | 11/2003 | Mark et al. | |
| 2004/0049217 | A1 | 3/2004 | Ross et al. | |
| 2004/0077938 | A1 * | 4/2004 | Mark | A61B 17/3403 600/411 |
| 2004/0267086 | A1 | 12/2004 | Anstadt et al. | |
| 2005/0027210 | A1 | 2/2005 | Miller | |
| 2005/0065517 | A1 * | 3/2005 | Chin | A61B 17/3421 606/86 A |
| 2005/0085798 | A1 | 4/2005 | Hofmann et al. | |
| 2005/0103607 | A1 | 5/2005 | Mezhinsky | |
| 2005/0154407 | A1 | 7/2005 | Simpson | |
| 2005/0273019 | A1 * | 12/2005 | Conway | A61B 5/15074 600/576 |
| 2005/0277970 | A1 | 12/2005 | Norman et al. | |
| 2006/0025749 | A1 * | 2/2006 | Moenning | A61M 39/02 604/506 |
| 2006/0135882 | A1 | 6/2006 | Bleich | |
| 2006/0241343 | A1 | 10/2006 | Miller et al. | |
| 2007/0073226 | A1 | 3/2007 | Polidoro et al. | |
| 2007/0073326 | A1 | 3/2007 | Miller et al. | |
| 2007/0149977 | A1 | 6/2007 | Heavener | |
| 2007/0167736 | A1 * | 7/2007 | Dietz | A61B 10/0275 600/411 |
| 2007/0208271 | A1 * | 9/2007 | Voegele | A61B 10/0275 600/564 |
| 2007/0208272 | A1 * | 9/2007 | Voegele | A61B 10/0275 600/564 |
| 2007/0270714 | A1 | 11/2007 | Cushner et al. | |
| 2007/0283970 | A1 | 12/2007 | Mohr et al. | |
| 2008/0045964 | A1 | 2/2008 | Mishra | |
| 2008/0114387 | A1 | 5/2008 | Hertweck et al. | |
| 2008/0188767 | A1 | 8/2008 | Oaki et al. | |
| 2008/0200834 | A1 * | 8/2008 | Mark | A61B 17/3468 600/566 |
| 2008/0234720 | A1 | 9/2008 | Chang et al. | |
| 2008/0243105 | A1 | 10/2008 | Horvath | |

(56) References Cited

U.S. PATENT DOCUMENTS

| | | | |
|---|---|---|---|
| 2008/0249366 A1 | 10/2008 | Gruber et al. | |
| 2008/0249553 A1 | 10/2008 | Gruber et al. | |
| 2008/0262476 A1 | 10/2008 | Krause et al. | |
| 2009/0112118 A1 | 4/2009 | Quick, Jr. et al. | |
| 2009/0124975 A1 | 5/2009 | Oliver et al. | |
| 2009/0131819 A1 | 5/2009 | Ritchie et al. | |
| 2009/0171243 A1 | 7/2009 | Hibner et al. | |
| 2009/0253967 A1* | 10/2009 | Gill | A61B 1/00165 600/249 |
| 2009/0270812 A1 | 10/2009 | Litscher et al. | |
| 2009/0281477 A1 | 11/2009 | Mikus et al. | |
| 2010/0152615 A1 | 6/2010 | Mark et al. | |
| 2010/0152758 A1* | 6/2010 | Mark | A61B 10/0275 606/171 |
| 2010/0249817 A1 | 9/2010 | Mark | |
| 2010/0292607 A1 | 11/2010 | Moore et al. | |
| 2011/0056902 A1 | 3/2011 | Cognard | |
| 2011/0190802 A1 | 8/2011 | Mark et al. | |
| 2011/0281350 A1 | 11/2011 | Schowalter et al. | |
| 2011/0282239 A1 | 11/2011 | Conlon et al. | |
| 2011/0282372 A1 | 11/2011 | Schowalter et al. | |
| 2011/0313316 A1* | 12/2011 | Ranpura | A61B 10/0275 600/566 |
| 2012/0071748 A1* | 3/2012 | Mark | A61B 17/3417 600/411 |
| 2012/0289816 A1* | 11/2012 | Mark | A61B 1/0607 600/411 |
| 2013/0211316 A1 | 8/2013 | Wilcox et al. | |
| 2013/0211321 A1* | 8/2013 | Dubois | A61M 13/00 604/26 |
| 2017/0265893 A1* | 9/2017 | Mark | A61B 17/3423 |

FOREIGN PATENT DOCUMENTS

| | | | |
|---|---|---|---|
| EP | 0497520 | A1 | 8/1992 |
| EP | 1201210 | A1 | 5/2002 |
| EP | 1714617 | A1 | 10/2006 |
| EP | 1815798 | A2 | 8/2007 |
| EP | 1859742 | A1 | 11/2007 |
| EP | 1915949 | A1 | 4/2008 |
| WO | 9418894 | A1 | 9/1994 |
| WO | 9613845 | A1 | 5/1996 |
| WO | 9846147 | A1 | 10/1998 |
| WO | 0022994 | A1 | 4/2000 |
| WO | 0230303 | A1 | 4/2002 |
| WO | 03045290 | A1 | 6/2003 |
| WO | 2006123312 | A1 | 11/2006 |
| WO | 2007002230 | A1 | 1/2007 |
| WO | 2007005507 | A2 | 1/2007 |
| WO | 2007034416 | A2 | 3/2007 |
| WO | 2007047380 | A2 | 4/2007 |
| WO | 2007062412 | A2 | 5/2007 |
| WO | 2008023193 | A2 | 2/2008 |
| WO | 2008058157 | A2 | 5/2008 |
| WO | 2011146682 | A1 | 11/2011 |

OTHER PUBLICATIONS

Publication entitled: "EndoFlex Steerable Nucelotome for Endoscopic Microdisectomy", published by Surgical Dynamics, 1993.
Publication entitled: "Nucleotome Flex II for Automated Percuaneous Lumbar Discectomy", published by Surgical Dynamics, 1992.
Publication entitled: "Surgical Technique Nucelotome Micro I for Automated Open Lumbar Discectomy", published by Surgical Dynamics, 1992.
Publication entitled; "Micro II Bendable Nucelotome for Open Lumbar Discectomy", published by Surgical Dynamics, 1993.
Publication entitled, "Positron Emission Tomography-Guided Volumetric Resection of Supratentorial High-Grade Glimoas: A Survival Analysis in 66 Consecutive Patients" by Benoit J.M. Pirotte, M.D., Ph.D. et al.—Published in Clinical Studies Neurosurgery, vol. 64, No. 3, Mar. 2009.
Publication entitled, "New Device Approval—AristaTM AH Absorbable Hemostat—P050038", Published in FDA U.S. Food and Drug Administration, dated Apr. 13, 2009.
Publication entitled: "Precision Begins with a Linemaster Switch", published by Linemaster Switch Corp., 2000.
Publication entitled: "Heavy Duty Foot Potentiometer", published at www.herga.com, Herga Electric Ltd. Apr. 30, 2009.
Publication entitled: "Vacuum Generators, How the E-Vac Works", published in Exair Corporation, Copyright 2009.
Publication entitled: "An Automated Tumor Resection Device for Neurological Surgery," authors, Martin L. Lazar, M. D., et al.; published by Texas Neurological Institute at Dallas, vol. 3, No. 3 (1978).
Publication entitled, "Automated Tumor Extraction Device for Neurological Surgery," by Wang et al.; published by Journal of Clinical Engineer, Apr.-Jun. 1979.
Keller, D.M., PhD, "Patients With Newly Diagnosed Glioblastoma Benefit Even From Less Than Total Resection," (May 31, 2010) http://www.medscape.com/viewarticle/721786.
Nakano, T., et al., Endoscopic Treatment for Deep-Seated or Multiple Intraparenchymal Tumors: Technical Note; (Minim Invas Neurosurg (2009)).
Compton, C.C., The Surgical Specimen is the Personalized Part of Personalized Cancer Medicine; Society of Surgical Oncology (2009).
Schlomm, T., et al., "Marked Gene Transcript Level Alterations Occur Early During Radical Prostatectomy," European Urology 53 (2008) 333-346.
Lin, D.W., et. al., "Influence of Surgical Manipulation on Prostate Gene Expression: Implications for Molecular Correlates of Treatment Effects and Disease Prognosis," Journal of Clinical Oncology, vol. 24, No. 23, (Aug. 10, 2006).
Spruessel, A., et al., "Tissue ischemia time affects gene and protein expression patterns within minutes following surgical tumor excision," Research Report, Center for Cancer Research at Israelitic Hospital, vol. 36, No. 6, (2004).
Dash, A., et al., "Changes in Differential Gene Expression because of Warm Ischemia Time of Radical Prostatectomy Specimens," American Journal of Pathology, vol. 161. No. 5, (Nov. 2002).
Nishihara, T., et al., "A transparent sheath of endoscopic surgery and its application in surgical evacuation of spontaneous intracerebral hematomas," J. Neurosurg. 92: 1053-1055 (2000).
Signoretti, S., et al., "Tissue-Based Research in Kidney Cancer: Current Challenges and Future Directions," Review Clin Cancer Res 2008; 14(12) Jun. 15, 2008.
Naylor, Stephen, et al., "Unraveling human complexity and disease with systems biology and personalized medicine," Personalized Medicine (2010).
Article, "Patient-Specific Brain Cancer 'Vaccine' May Help Prevent Recurrence," Health News, US Academic Health Center, University of Cincinnati, Jul. 9, 2008.
Lesniak, Jaciej S., "Targeted therapy for malignant glioma: neural stem cells," ISSN 1473-7175 (2006).
Human, Katy, "Using personalized vaccines, researchers enlist the immune system to oust tumors," www.curetoday.com (2010).
Park, Alice, "A Shot at Cancer," Time (Sep. 3, 2009).
Author Unknown, "The World's Thinnest, Smallest & Strongest Heat Shrink Tubing," Advanced Polymers, Inc., date unknown, 2 pages.
Arthur Hill, M.D., and Ming Si, M.D., "Hemostatic Agents, Sealants, and Tissue Adhesives," University of California, San Francisco, date unknown, 29 pages.
Storrs, Carina, "Trained Cancer Killer, Medicine Harnesses the Might of the Immune System to Defeat Prostate Cancer," Popular Science, Jan. 21, 2011 https://www.popsci.com/science/article/2011-01/instant-expert-vaccine-cancer/.

* cited by examiner

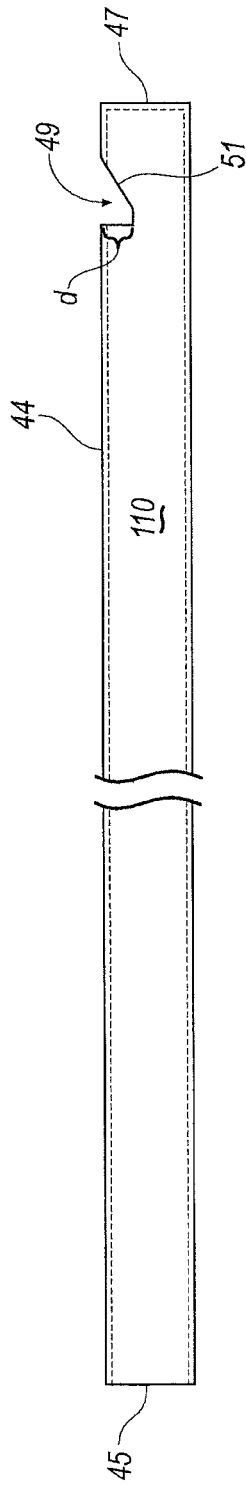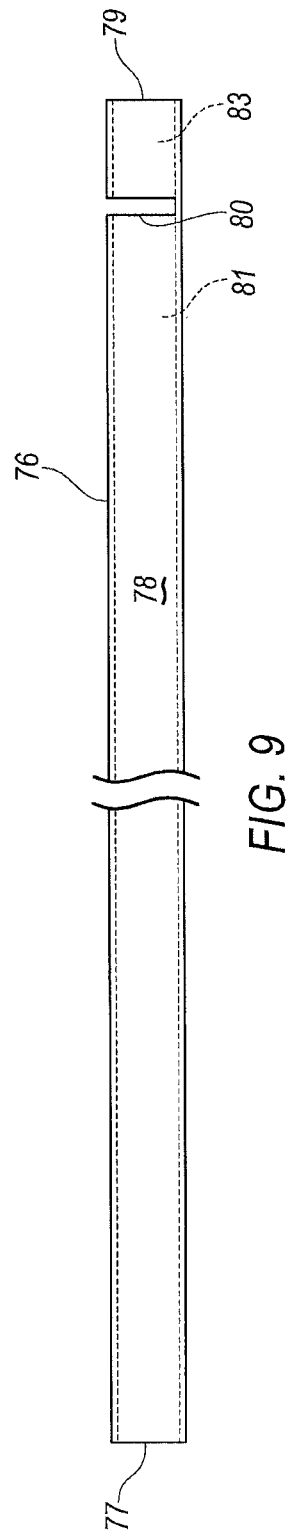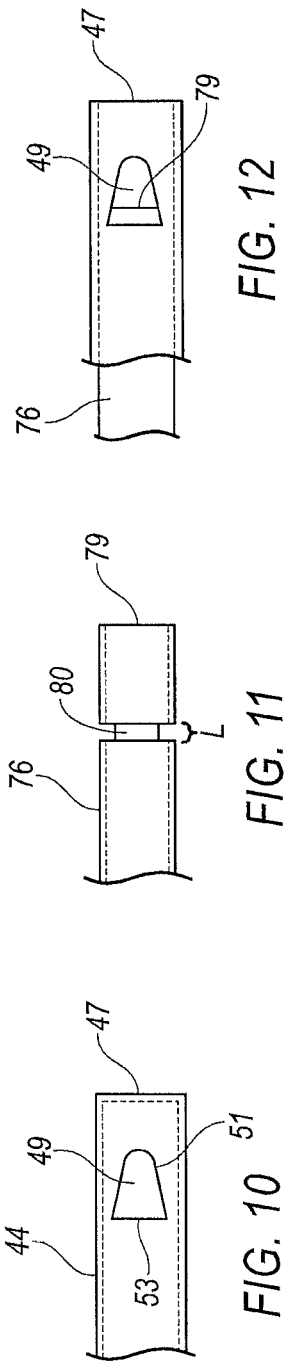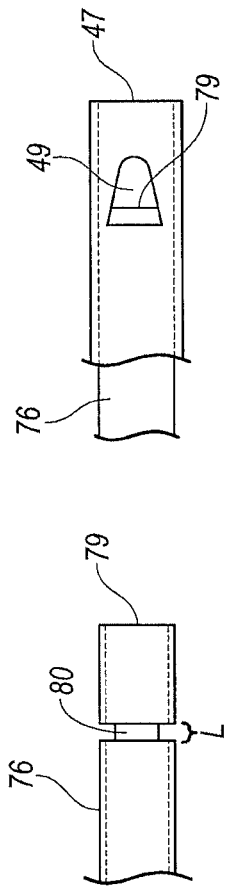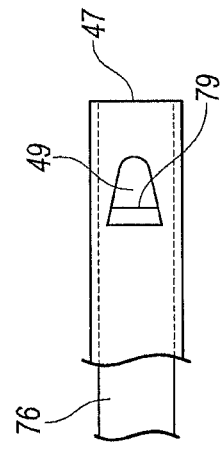

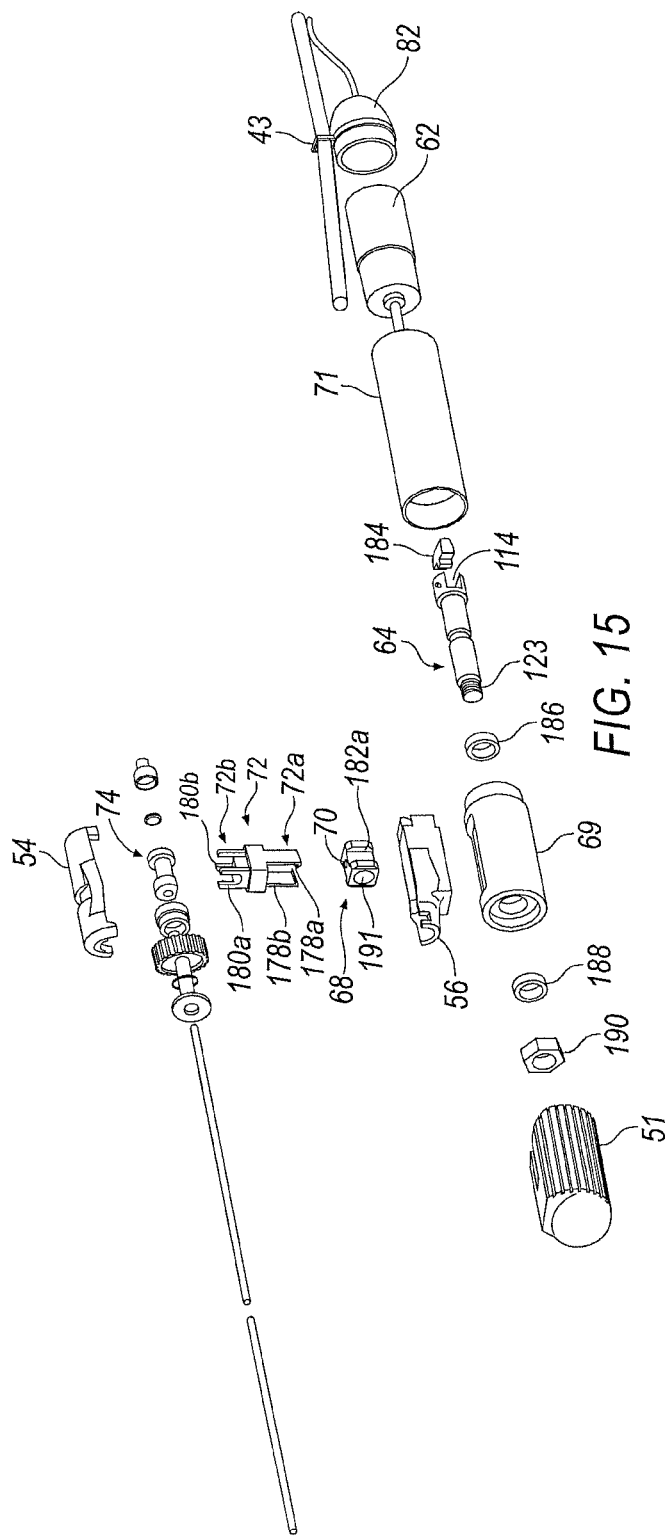

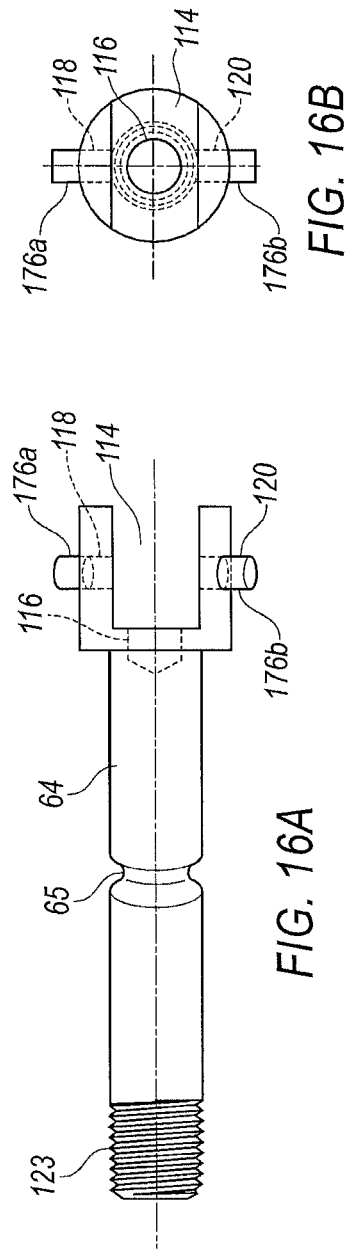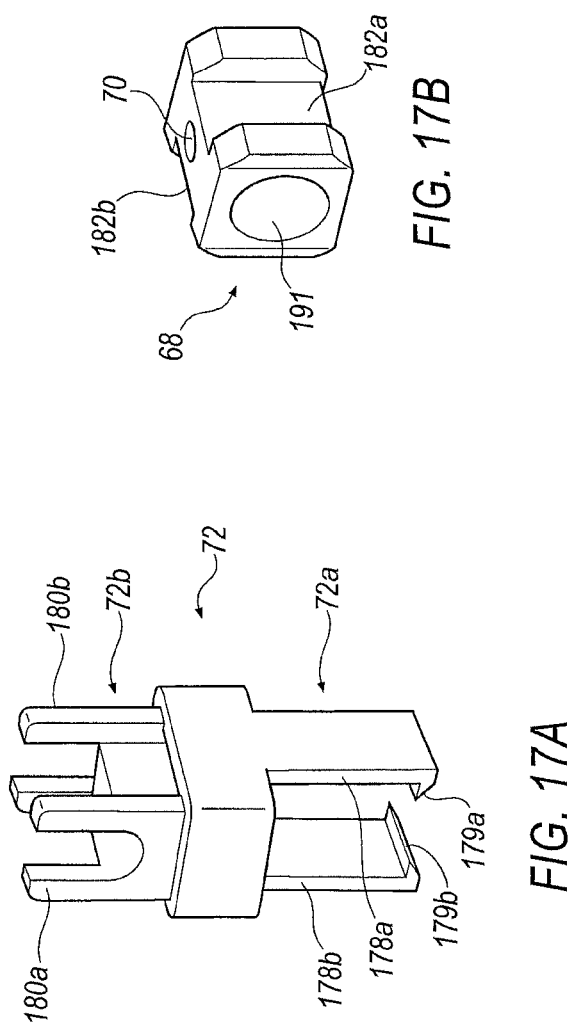

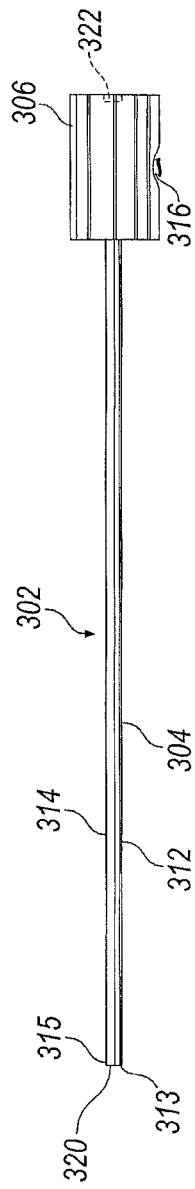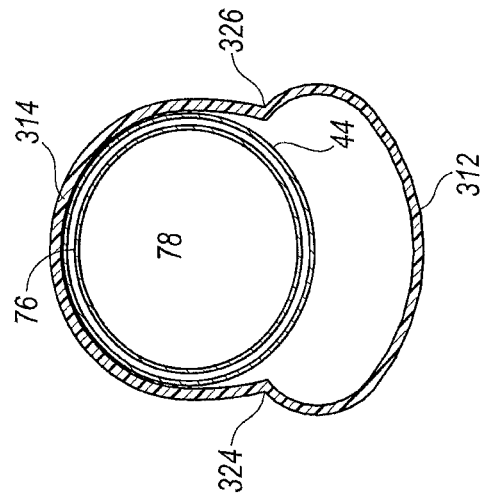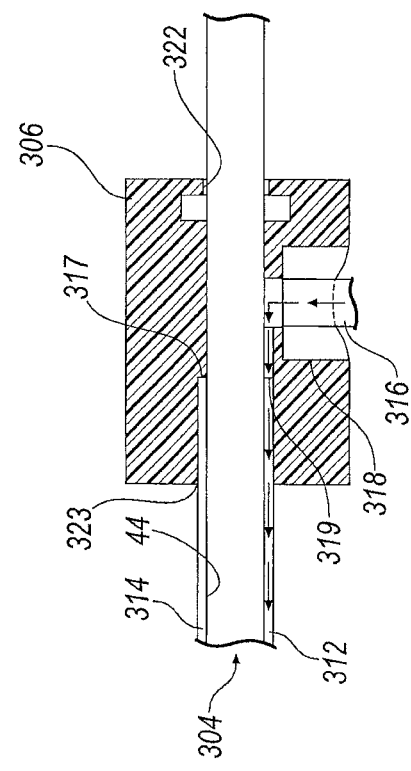

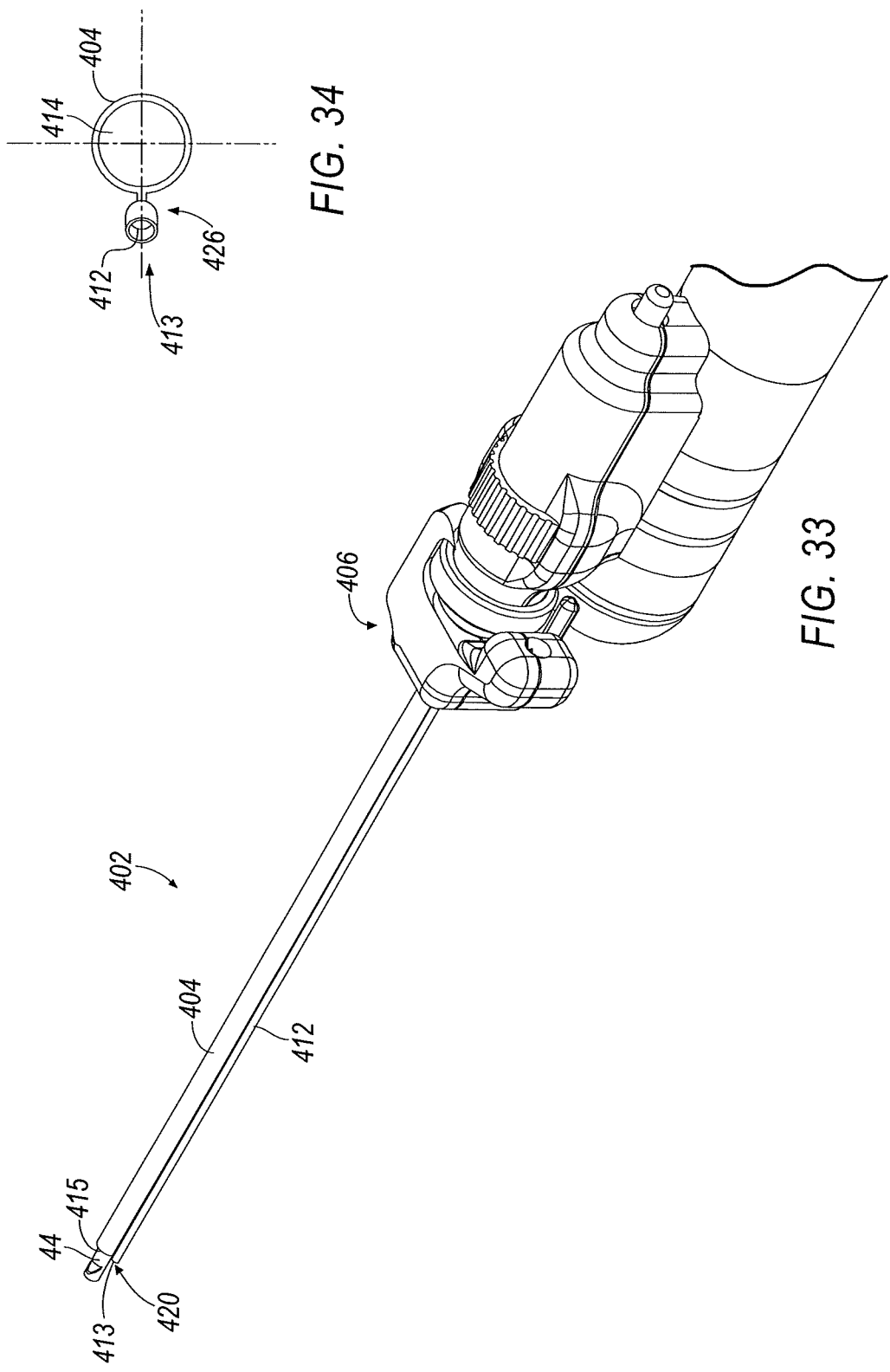

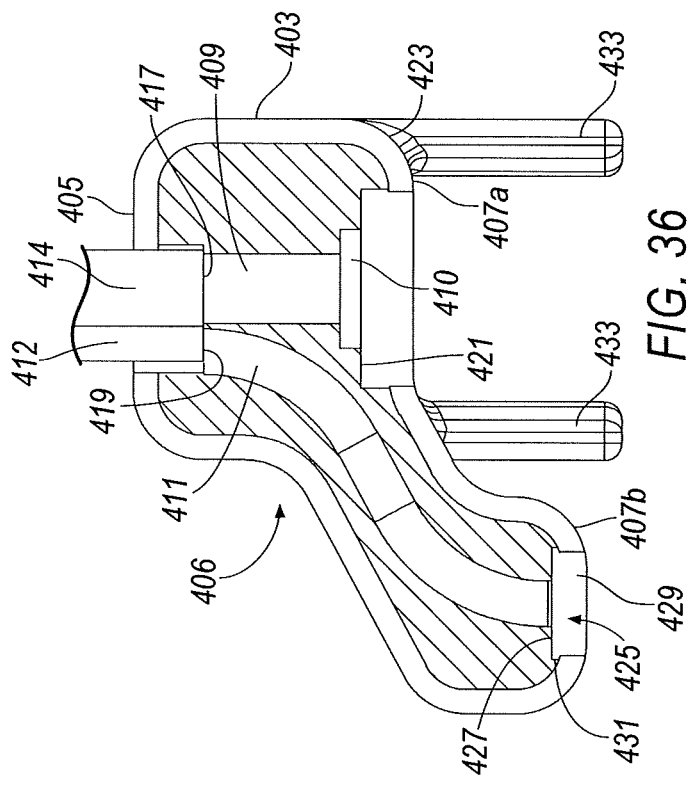
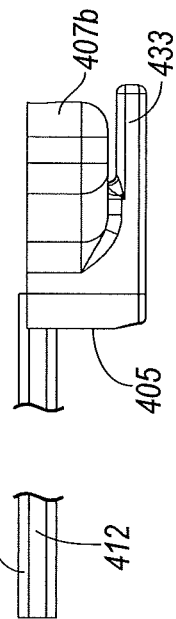
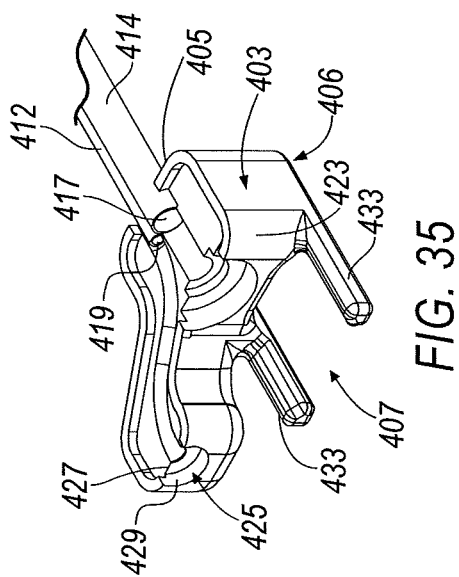
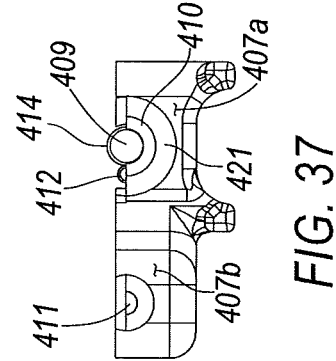
FIG. 36
FIG. 38
FIG. 35
FIG. 37

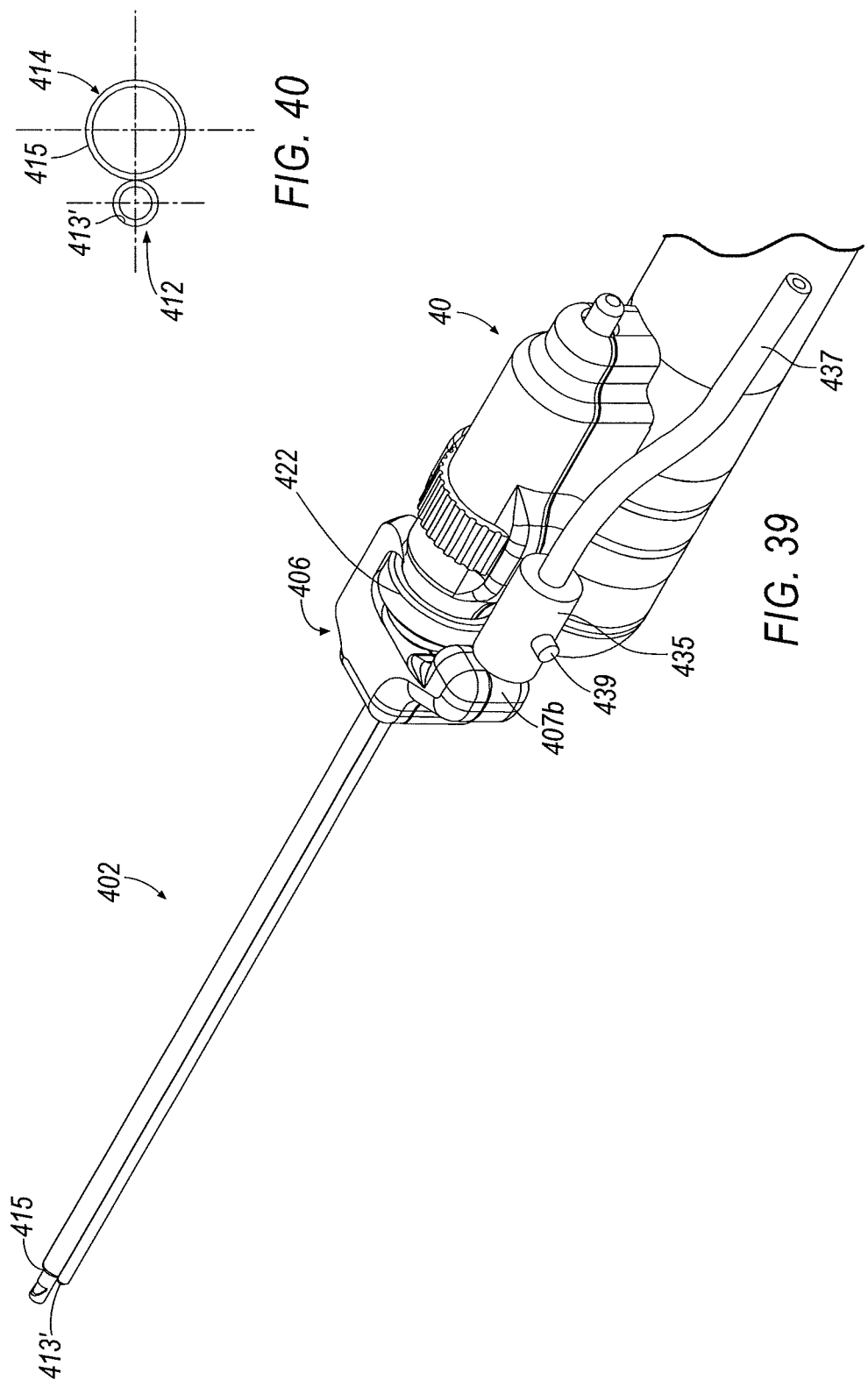

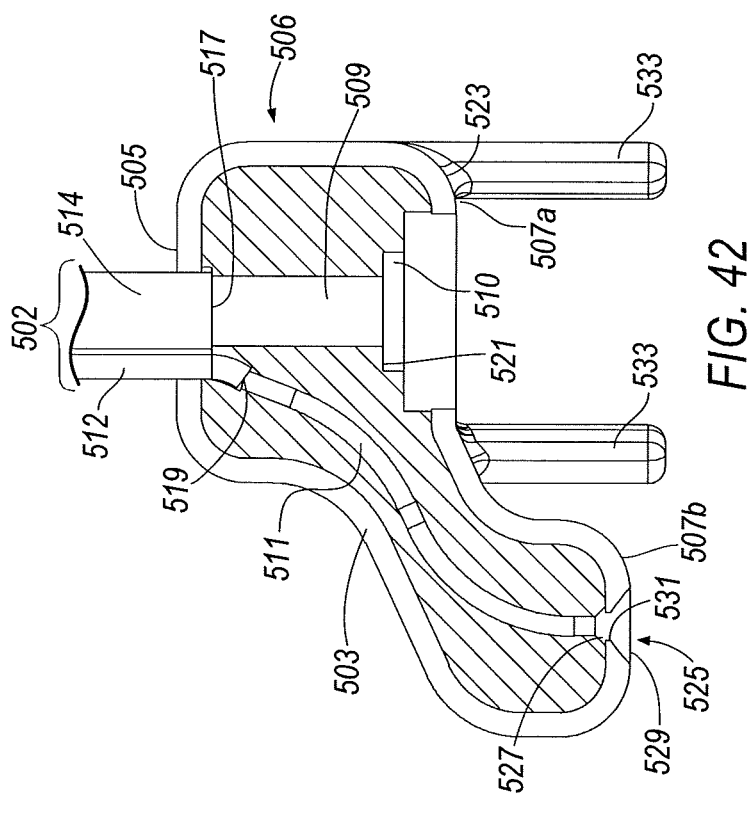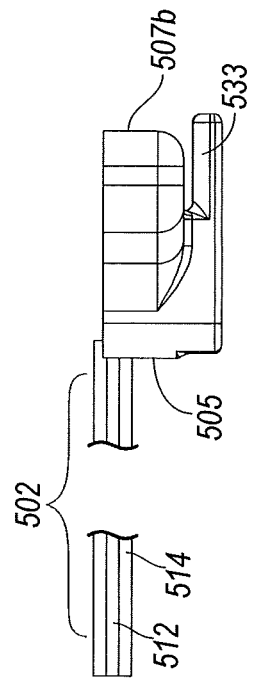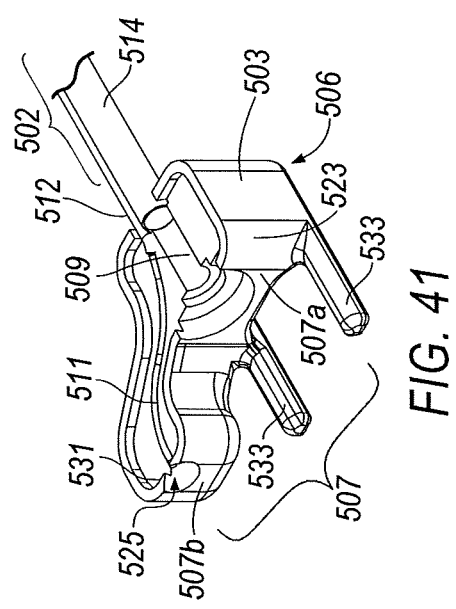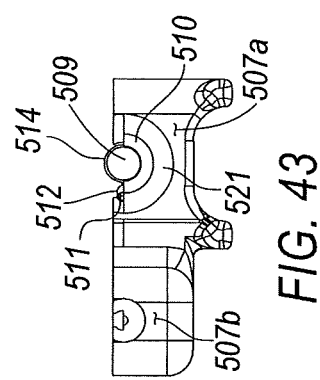

TISSUE REMOVAL DEVICE WITH ADJUSTABLE DELIVERY SLEEVE FOR NEUROSURGICAL AND SPINAL SURGERY APPLICATIONS

CROSS-REFERENCE TO RELATED APPLICATIONS

This application is a continuation of U.S. application Ser. No. 13/269,339 filed on Oct. 7, 2011, now U.S. Pat. No. 10,080,578 issued Sep. 25, 2018, which is a continuation-in-part of U.S. application Ser. No. 12/475,258 filed on May 29, 2009, now U.S. Pat. No. 9,216,031 issued Dec. 22, 2015, which is a continuation-in-part of U.S. application Ser. No. 12/435,724, filed on May 5, 2009, now U.S. Pat. No. 8,460,327 issued Jun. 11, 2013, which is a continuation-in-part of U.S. application Ser. No. 12/404,407, filed on Mar. 16, 2009, now U.S. Pat. No. 8,496,599 issued Jul. 30, 2013, which is a continuation-in-part of U.S. application Ser. No. 12/391,579, filed on Feb. 24, 2009, now U.S. Pat. No. 8,702,738 issued Apr. 22, 2014, which is a continuation-in-part of U.S. application Ser. No. 12/389,447, filed on Feb. 20, 2009, now U.S. Pat. No. 9,655,639 issued May 23, 2017, which is a continuation-in-part of U.S. application Ser. No. 12/336,054, filed Dec. 16, 2008, now U.S. Pat. No. 8,430,825 issued Apr. 30, 2013, and U.S. application Ser. No. 12/336,086, filed Dec. 16, 2008, now U.S. Pat. No. 8,657,841 issued Feb. 25, 2014, each of which is hereby incorporated by reference in their entirety.

TECHNICAL FIELD

The present disclosure relates to tissue cutting devices, in particular, tissue cutting devices that include a delivery sleeve and which are suited for neurosurgical and spinal surgical procedures.

BACKGROUND

Various abnormalities of the neurological system, such as brain and spinal tumors, cysts, lesions, or neural hematomas, can cause severe health risks to patients afflicted by them, including deterioration in motor skills, nausea or vomiting, memory or communication problems, behavioral changes, headaches, or seizures. In certain cases, resection of abnormal tissue masses is required. However, given the complexity and importance of the neurological system, such neurosurgical procedures are extremely delicate and must be executed with great precision and care. Some known tissue cutting systems lack the ability to deliver fluids and ancillary devices to or near a surgical site. Other known systems lack the ability to accurately and effectively adjust the fluid delivery location relative to the tissue cutting location. In addition, it is sometimes desirable to operate a tissue cutting device as an aspiration wand. Many systems are unable to operate in such a mode or are unable to accurately control adjust the extent of aspiration with precision. Thus, a need has arisen for a tissue cutting system that addresses the foregoing issues.

BRIEF DESCRIPTION OF THE DRAWINGS

Embodiments of the present disclosure will now be described by way of example in greater detail with reference to the attached figures, in which:

FIG. 8 is a broken side elevation view of the outer cannula of the tissue cutting device of FIG. 1;

FIG. 9 is a broken side elevation view of the inner cannula of the tissue cutting device of FIG. 1;

FIG. 10 is a top plan view of a portion of the outer cannula of the tissue cutting device of FIG. 1 with the inner cannula removed from the outer cannula;

FIG. 11 is a top plan view of a portion of the inner cannula of the tissue cutting device of FIG. 1;

FIG. 12 is a top plan view of a portion of the outer cannula and inner cannula of FIG. 1 depicting the inner cannula inserted into the outer cannula;

FIG. 15 is an exploded assembly view of the tissue cutting device of FIG. 1;

FIG. 16a is a side elevation view of a cam of the tissue cutting device of FIG. 1;

FIG. 16b is an end elevation view of the cam of FIG. 16a;

FIG. 17a is a perspective view of a cam transfer mechanism of the tissue cutting device of FIG. 1;

FIG. 17b is a perspective view of a cam follower of the tissue cutting device of FIG. 1;

FIG. 28 is a side elevational view of the irrigation sleeve of FIG. 1;

FIG. 29 is a partial close-up, longitudinal cross-sectional view of the delivery sleeve, outer cannula and inner cannula of FIG. 1;

FIG. 30 is a transverse cross-sectional view taken along line 30-30 in FIG. 29;

FIG. 33 is a partial perspective view of an alternative embodiment of a delivery sleeve mounted on a tissue cutting device.

FIG. 34 is an exemplary configuration of an end view of the delivery sleeve of FIG. 33.

FIG. 35 is a perspective view of a hub for supporting the delivery sleeve of FIG. 33.

FIG. 36 is a cross-sectional view of the hub of FIG. 35.

FIG. 37 is an end view of the hub of FIG. 35.

FIG. 38 is side elevational view of the hub of FIG. 35.

FIG. 39 is a partial perspective view of the delivery sleeve mounted on a tissue cutting device connected to a fluid supply.

FIG. 40 is an end view of the delivery sleeve of FIG. 39.

FIG. 41 is a perspective view of an alternative hub for supporting a delivery sleeve.

FIG. 42 is a cross-sectional view of the hub of FIG. 41.

FIG. 43 is an end view of the hub of FIG. 41.

FIG. 44 is side elevational view of the hub of FIG. 41.

DETAILED DESCRIPTION

Figure 1:
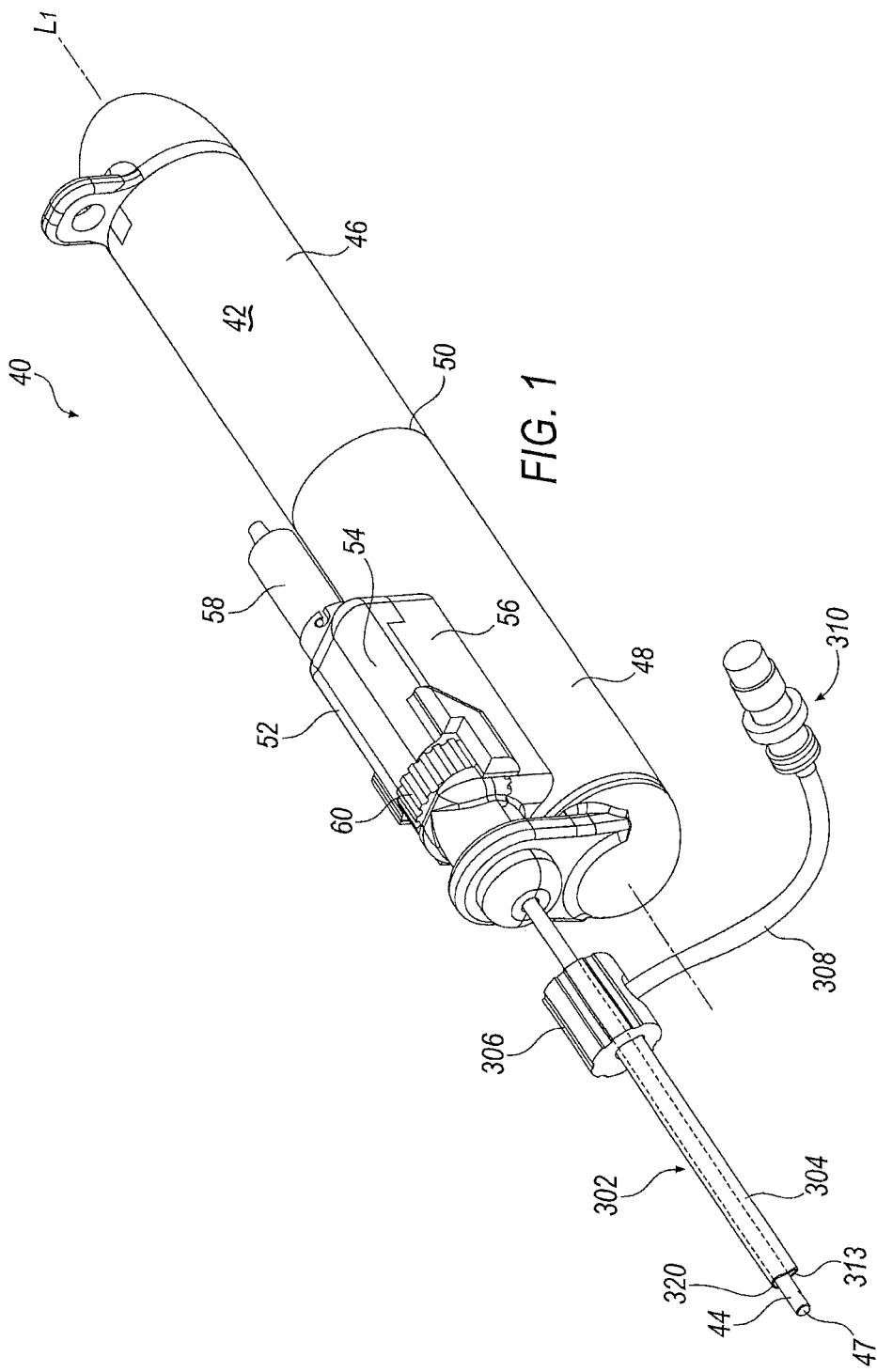
FIG. 1 is a perspective view of a tissue cutting device including a fluid supply sleeve in accordance with a first embodiment.

Referring now to the discussion that follows and also to the drawings, illustrative approaches to the disclosed systems and methods are shown in detail. Although the drawings represent some possible approaches, the drawings are not necessarily to scale and certain features may be exaggerated, removed, or partially sectioned to better illustrate and explain the present disclosure. Further, the descriptions set forth herein are not intended to be exhaustive or otherwise limit or restrict the claims to the precise forms and configurations shown in the drawings and disclosed in the following detailed description.

Described herein are tissue cutting devices that are suited for neurosurgical applications such as the removal of spine and brain tissue. The devices are configured with a delivery sleeve that is disposed on an outer cannula and selectively positionable along the length of the outer cannula. As a result, the tissue cutting devices can simultaneously provide, without the need for removal of the tissue cutting device from the surgical site, delivery of fluids such as irrigants, hemostatic agents, and tissue sealants to a surgical site and other devices complementary to the tissue removal device and accretive to the surgical procedure. They can also be used to selectively adjust the area of the outer cannula aperture through which the aspiration is delivered through to the tissue.

Referring to FIG. 1, a tissue cutting device 40 includes a handpiece 42 and an outer cannula 44. In one exemplary embodiment, handpiece 42 is generally cylindrical in shape and is preferably sized and shaped to be grasped with a single hand. Handpiece 42 includes a lower housing 50 which comprises a proximal section 46 and distal section 48. Lower housing 50 comprises a proximal-most housing portion 82 (FIGS. 2 and 3) that is connected to a motor housing 71, and a cam housing 69 that is connected to motor housing 71. A front housing section 51 is connected to cam housing 69. Upper housing 52 is also provided. A tissue collector 58 may be operatively connected to upper housing 52 (as will be explained in further detail below). A rotation dial 60 for rotating the outer cannula 44 with respect to handpiece 42 is also mounted to upper housing 52.

Figure 2:
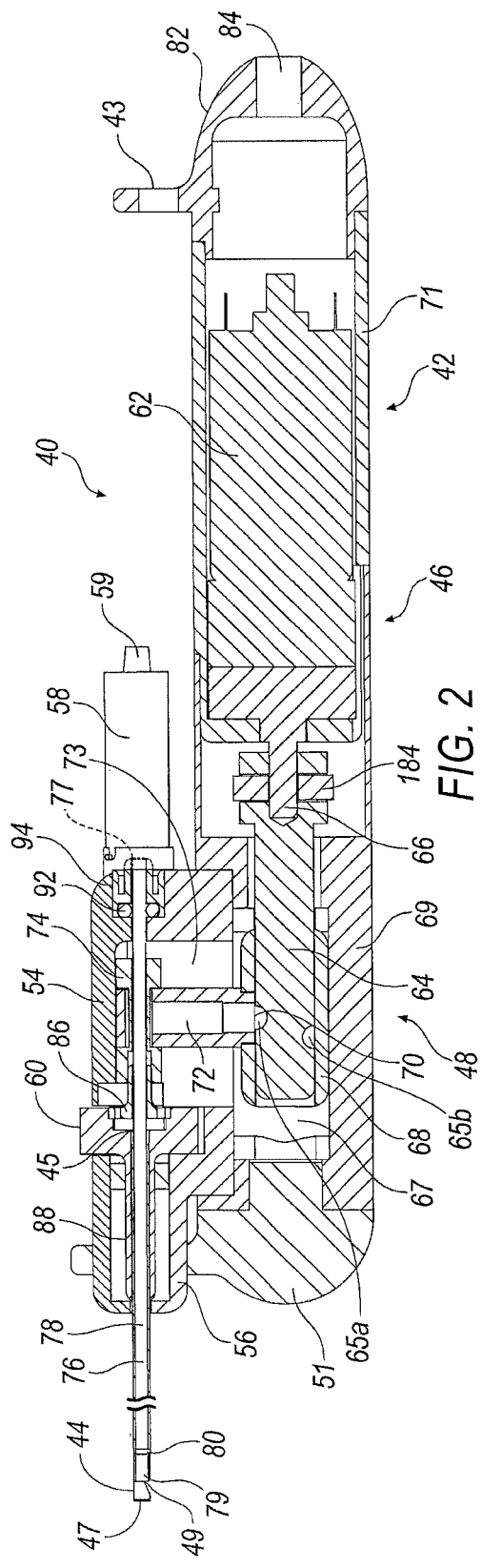
FIG. 2 is a cross-sectional view of the tissue cutting device of FIG. 1 depicting an inner cannula in a first relative position with respect to an outer cannula in which the inner cannula's distal end is located proximally of the outer cannula's distal end.
Figure 3:
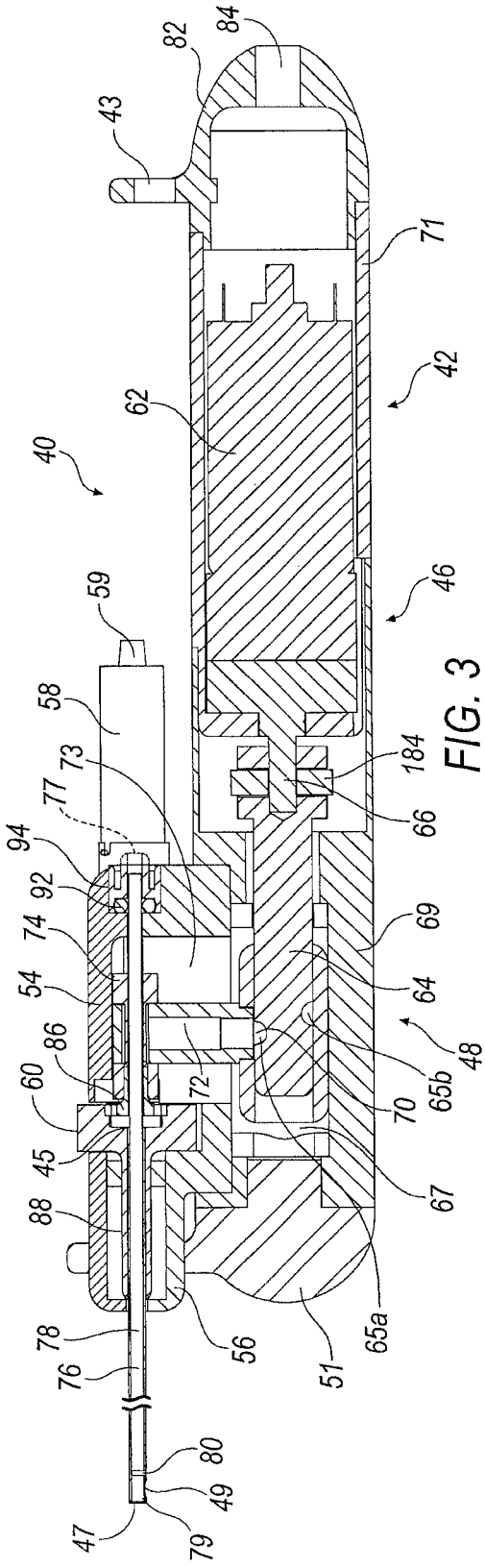
FIG. 3 is a cross-sectional view of the tissue cutting device of FIG. 1 depicting the inner cannula in a second relative position with respect to the outer cannula in which the inner cannula's distal end is located at the distal end of the outer cannula.
Figure 20:
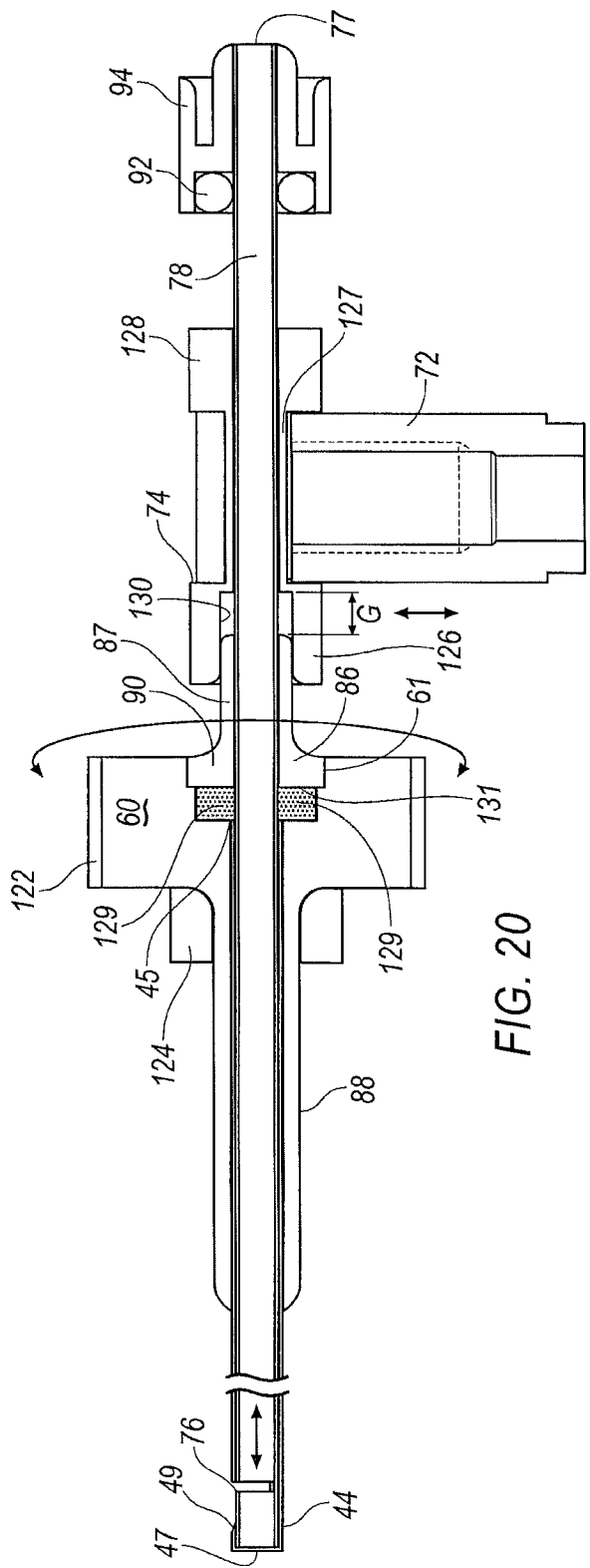
FIG. 20 is a side elevation view of an inner and outer cannula assembly of the tissue cutting device of FIG. 1.

As best seen in FIGS. 2, 3, and 20, outer cannula 44 includes an open proximal end 45, a closed distal end 47, and a distal opening 49 proximate distal end 47. Tissue cutting device 40 further comprises an inner cannula 76 which is partially disposed in an outer cannula lumen 110 (FIG. 8). Inner cannula 76 is configured to reciprocate within outer cannula lumen 110 and to cut tissue samples entering outer cannula 44 via outer cannula distal opening 49, as will be described in greater detail below. Inner cannula 76 reciprocates between a proximal position, which is depicted in FIG. 2 and a distal position which is depicted in FIG. 3. Inner cannula 76 includes an open proximal end 77 and an open distal end 79. Distal end 79 is preferably configured to cut tissue, and in preferred embodiments is capable of cutting neurological system tissues such as those from the brain or spine. In one exemplary embodiment, inner cannula distal end 79 is beveled in a radially inward direction to create a sharp circular tip and facilitate tissue cutting.

Outer cannula 44 is not translatable, and its position with respect to handpiece 42 along the direction of the longitudinal axis of handpiece 42 remains fixed. Delivery sleeve 302 (FIG. 1) is selectively attachable to outer cannula 44 and allows fluids and devices to be provided proximate a surgical site. Delivery sleeve 302 has a proximal hub 306 and a distal end 320. An outer cannula opening 322 is provided at the proximal end of delivery sleeve 302. Elongated channel section 304 is connected to proximal hub 306 and projects distally away from it. Distal end 320 of delivery sleeve 302 is the distal end of the elongated channel section 304. In FIG. 1, delivery sleeve 302 is shown in an installed condition on outer cannula 44. In the depicted installed condition, delivery sleeve 302 is selectively positionable along the length of outer cannula 44.

In FIGS. 2-3, delivery sleeve 302 is not shown for ease of viewing. Motor 62 is disposed in proximal lower housing section 46 of handpiece 42 and is operably connected to inner cannula 76 to drive the reciprocation of inner cannula 76 within outer cannula lumen 110. Motor 62 may be a reciprocating or rotary motor. In addition, it may be electric or hydraulic. However, in the embodiment of FIGS. 2 and 3, motor 62 is a rotary motor, the rotation of which causes inner cannula 76 to reciprocate within outer cannula lumen 110.

Motor 62 is housed in motor housing 71, which defines a portion of lower housing proximal section 46. Motor 62 is connected to an inner cannula drive assembly 63 which is used to convert the rotational motion of motor 62 into the translational motion of inner cannula 76. At its proximal end, motor housing 71 is connected to proximal-most housing portion 82, which includes a power cable port 84 and a hose connector 43, which in the exemplary embodiment of FIG. 3 is an eyelet. Hose connector 43 provides a means of securely retaining a vacuum system hose to handpiece 42, thereby allowing vacuum to be supplied to tissue collector 58.

Inner cannula driver assembly 63 (not separately shown in figures) comprises a cam 64, a cam follower 68, a cam transfer 72, and a cannula transfer 74. Cam 64 is a generally cylindrical structure and is shown in detail in FIGS. 16A and 16B. A groove or channel 65 is defined in the surface of cam 64. In one exemplary embodiment, groove 65 is continuous and circumscribes the perimeter of cam 64 but is not oriented perpendicularly to the longitudinal axis of cam 64, i.e., groove 65 is angled with respect to the cam axis. Opposing points on groove 65 such as points 65a and 65b (FIGS. 2 and 3) define pairs of "apexes" that are spaced apart along the longitudinal axis of the cam, i.e., the groove extends along a portion of the length of the cam. Cam 64 also includes a proximal opening 114 (FIG. 16a) for receiving a motor shaft and a proximal recess 116 into which a shaft may be snugly received. Holes 118 and 120 are provided for mounting position indicators that cooperate with a position sensor to determine the angular position of cam 64, and correspondingly, the linear position of inner cannula 76 within the outer cannula lumen 110, as discussed below.

Cam follower 68 is depicted in detail in FIG. 17B. Cam follower 68 is a generally rectangular block shaped structure with a hollow interior in which cam 64 is partially disposed. Cam follower 68 also includes a hole 70 in its upper face in which a ball bearing (not shown) is seated. The ball bearing rides in cam groove 65 and engages cam transfer 72. As a result, when cam 64 rotates, cam follower 68 translates along the length of handpiece 42. Cam follower 68 also includes lateral slots 182a and 182b that cooperatively engage corresponding members 178a, 178b from cam transfer 72.

Cam follower 68 is disposed within a cam chamber 67 formed in cam housing 69. Cam 64 is partially disposed in cam chamber 67 and extends proximally therefrom to engage motor 62. Cam housing 69 comprises part of distal portion 48 of handpiece 42. Cam 64 does not reciprocate within cam chamber 67 and instead merely rotates about its own longitudinal axis. However, cam follower 68 reciprocates within cam chamber 67 along the direction of the length of handpiece 42. Cam follower 68 is open at its proximal end to receive cam 64. As shown in FIGS. 15 and 16A, cam 64 may optionally include a threaded distal end 123 that projects through a distal opening 191 (FIG. 17b) in cam follower 68 and which engages a nut 190 (FIG. 15) to prevent reciprocation of cam 64 relative to cam housing 69. Proximal cam bearing 186 and distal cam bearing 188 (FIG. 15) may also be provided to support cam 64 as it rotates within cam housing 69.

Cam transfer 72 extends from cam chamber 67 into a cam transfer chamber 73 formed in upper housing 52. As best seen in FIG. 17a, cam transfer 72 comprises a proximal end 72a that is attachable to cam follower 68 and a distal end 72b that is attachable to inner cannula 76 via cannula transfer 74. Proximal end 72a comprises a pair of spaced apart, downwardly extending members 178a and 178b, and distal end 72b comprises a pair of spaced apart upwardly extending members 180a and 180b. Downwardly extending members 178a and 178b are spaced apart in a direction that is perpendicular to the length of cam 64 and handpiece 42, while upwardly extending members 180a and 180b are spaced apart in a direction that is parallel to the length of cam 64 and handpiece 42. Cam follower slots 182a and 182b engage downwardly extending members 178a and 178b of cam transfer 72. Downwardly extending members 178a and 178b of cam transfer 72 may be resilient and may have engagement portions 179a and 179b on their free ends (e.g., hooks or clips) for securely engaging the bottom and side surfaces of cam follower 68.

As best seen in FIG. 20, cannula transfer 74 comprises a sleeve disposed about inner cannula 76. For ease of viewing, delivery sleeve 302 is not shown in FIG. 20. Cannula transfer 74 comprises a proximal end 128, middle section 127, and distal end 126. Upwardly extending members 180a and 180b of cam transfer 72 define fork-shaped structures that receive and cradle middle section 127 of cannula transfer 74. Distal end 126 and proximal end 128 of cannula transfer 74 are disposed outwardly of upwardly extending members 180a and 180b and are shaped to prevent relative translation between cam transfer 72 and cannula transfer 74. In the depicted embodiments, distal end 126 and proximal end 128 of cannula transfer 74 are enlarged relative to middle section 127 to abut the upwardly extending, fork-shaped members 182a and 182b, thereby preventing relative translation between cam transfer 72 and cannula transfer 74. As a result, when cam transfer 72 reciprocates along the length of handpiece 42, cannula transfer 74 reciprocates as well. Because it is affixed to inner cannula 76, when cannula transfer 74 reciprocates, it causes inner cannula 76 to reciprocate within outer cannula 44.

In one exemplary arrangement, motor 62 is a brushed DC motor and may be operably connected to cam 64 in a number of ways. In the embodiment of FIGS. 2 and 3, motor 62 includes a distally extending shaft 66 that extends into a proximal opening 114 and engages recess 116 (FIGS. 16A and B) defined in cam 64. Shaft 66 may be connected to cam 64 via a threaded connection, adhesive, or other known connection means. In an alternate implementation, depicted in FIG. 15, a separate cam coupler 184 is provided. Cam coupler 184 is seated in proximal opening 114 and has a width greater than the diameter of opening 114. Cam coupler 184 is also connected to motor shaft 66 such that rotation of shaft 66 causes cam coupler 184 to rotate, which in turn causes cam 64 to rotate therewith. One revolution of motor shaft 66 causes cam 64 to rotate by one revolution, which in turn causes inner cannula 76 to reciprocate by one complete stroke, i.e., from the position of FIG. 2 to the position of FIG. 3 and back to the position of FIG. 2.

Cam transfer 72 may be connected to cam follower 68 by mechanical means, adhesive means or other known connection means. In one exemplary embodiment, downwardly extending members 178a and 178b mechanically clip onto and removably engage cam follower 68. In another embodiment, cam transfer 72 is adhesively affixed to cam follower 68. In yet another embodiment, both mechanical and adhesive connections are used. The ball bearing (not shown) disposed in cam follower hole 70 traverses cam groove 65 as cam 64 rotates, causing cam follower 68 to reciprocate from the proximal position of FIG. 2 to the distal position of FIG. 3. As a result, cam transfer 72, cannula transfer 74 and inner cannula 76 translate between their respective proximal positions of FIG. 2 and their respective distal positions of FIG. 3 when motor 62 and cam 64 rotate.

Figure 14:
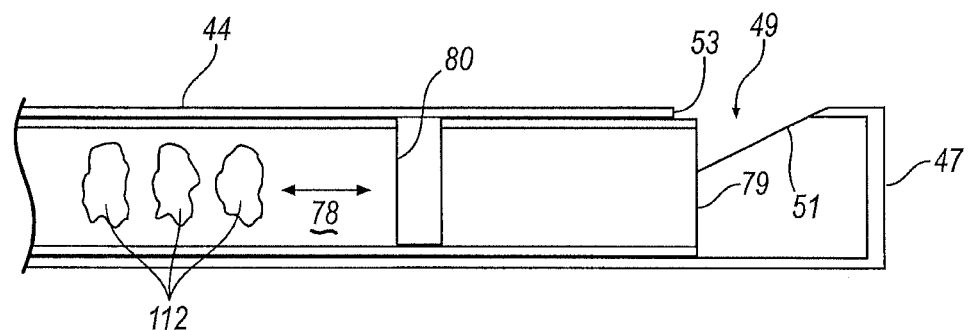
FIG. 14 is a partial cross-sectional view of a distal region of the outer cannula and the inner cannula of the tissue cutting device of FIG. 1, depicting the inner cannula in a second relative position with respect to the outer cannula.

Motor 62 is preferably selected to have a rotational speed that allows inner cannula 76 to reciprocate from the position of FIG. 2 to the position of FIG. 3 and back to the position of FIG. 2 at a rate of at least about 1,000 reciprocations/minute. Reciprocation rates of at least about 1,200 reciprocations/minute are more preferred, and reciprocation rates of at least about 1,500 reciprocations/minute are even more preferred. Reciprocation rates of less than about 2,500 reciprocations/minute are preferred. Reciprocation rates of less than about 2,000 are more preferred, and reciprocation rates of less than about 1,800 reciprocations/minute are even more preferred. As best seen in FIG. 14, the rates of reciprocation of device 40 allow tissue to be severed into "snippets" 112 which are relatively smaller than "slug" tissue samples obtained by many prior devices. As the reciprocation continues, a continuum of severed tissue snippets 112 is obtained.

As mentioned previously, outer cannula 44 includes an opening 49 for receiving tissue into outer cannula lumen 110. As best seen in FIGS. 8-12, opening 49 is preferably defined by a cutting edge 51 that is configured to sever tissue and a non-cutting edge 53 that is not configured to sever tissue. In certain exemplary implementations, cutting edge 53 has a radial depth "d" that is no greater than about 50% of the outer diameter of outer cannula 44. In one exemplary implementation, cutting edge 51 is beveled in a radially inward direction, non-cutting edge 53 is not beveled, and cutting edge 51 is located immediately distally of non-cutting edge 53. Inner cannula distal end 79 is preferably configured to cut tissue. In one exemplary embodiment, distal end 79 is beveled in a radially inward direction around the circumference of inner cannula 76 to provide a sharp edge. As tissue is received in outer cannula opening 49, it is compressed between inner cannula distal end 79 and outer cannula cutting edge 51, causing the received tissue to be severed from the surrounding tissue.

Tissue cutting device 40 is particularly well suited for use in cutting tough tissues such as spinal and brain tissues. Outer cannula 44 and inner cannula 76 comprise materials that are generally rigid, such as rigid plastics or metal. In one preferred implementation, both cannulas are constructed of stainless steel, and more preferably, 304SS typically used in medical grade instruments.

As best seen in FIGS. 9-14, to facilitate the cutting of tough tissues, inner cannula 76 includes a hinge 80. For ease of viewing, delivery sleeve 302 is not shown in FIGS. 9-14. Hinge 80 is located between inner cannula body section 81 which is located on the proximal side of hinge 80 and inner cannula cutting section 83 which is located on the distal side of hinge 80. In one exemplary arrangement, hinge 80 is a living hinge. As used herein, the term "living hinge" refers to a thin, flexible hinge that joins two relatively more rigid parts together. In one example, hinge 80 is a living hinge that is integrally formed with inner cannula body section 81 and inner cannula cutting section 83 by removing a portion of the circumference of the inner cannula 76 along a length L (FIG. 11). Hinge 80 allows cutting section 83 to pivot about hinge 80 as inner cannula 76 reciprocates within outer cannula 44. As inner cannula 76 translates in the distal direction, it contacts tissue received in outer cannula opening 49 and encounters progressively increasing resistance from the tissue as the tissue is urged in the distal direction. As the resisting force of the tissue increases, cutting section 83 pivots progressively more until a zero annular clearance is obtained between inner cannula distal end 79 and outer cannula opening 49. The received tissue is severed and aspirated in the proximal direction along inner cannula lumen 78 and received in tissue collector 58. Thus, inner cannula lumen 78 provides an aspiration path from the inner cannula distal end 79 to the inner cannula proximal end 77. Hinge 80 allows a generally zero annular clearance to be obtained between inner cannula distal end 79 and outer cannula opening 49 at cutting section 83 while not affecting the annular clearance between inner cannula body section 81 and outer cannula 44. This configuration maximizes tissue cutting while minimizing frictional losses that would otherwise occur due to the frictional engagement of the outer surface of inner cannula body section 81 and the inner surface of outer cannula 44 if a very small annular clearance between the outer cannula 44 and inner cannula 76 were present.

Outer cannula opening 49 may have a number of shapes. In certain examples, when outer cannula opening 49 is viewed in plan, it has a shape that is generally square, rectangular, trapezoidal, ovular, or in the shape of the letter "D." In certain other exemplary implementations, outer cannula opening 49 is configured to direct tissue so that it may be compressed as inner cannula 76 translates in the distal direction. In one exemplary embodiment, depicted in FIGS. 10 and 12, outer cannula opening 49 has a generally triangular shape when outer cannula opening 49 is viewed in plan. As FIGS. 10 and 12 indicate, when viewed in plan, the width of opening 49 in a direction transverse to the outer cannula longitudinal axis varies longitudinally along the length of outer cannula 44, and preferably narrows from the proximal to distal portions of opening 49. When viewed in side elevation, cutting edge 51 slopes in a radially outward direction moving distally along edge 51. As a result, as a tissue sample is distally urged within outer cannula opening 49 by the action of inner cannula 76, the tissue is increasingly compressed in the direction of the circumference of inner cannula 76 (or in the direction of the "width" of opening 49 when viewed in plan). To ensure complete cutting, inner cannula distal end 79 preferably travels to a position that is distal of outer cannula opening 49 during a tissue cutting operation, i.e., there is an inner cannula overstroke.

Figure 21A:
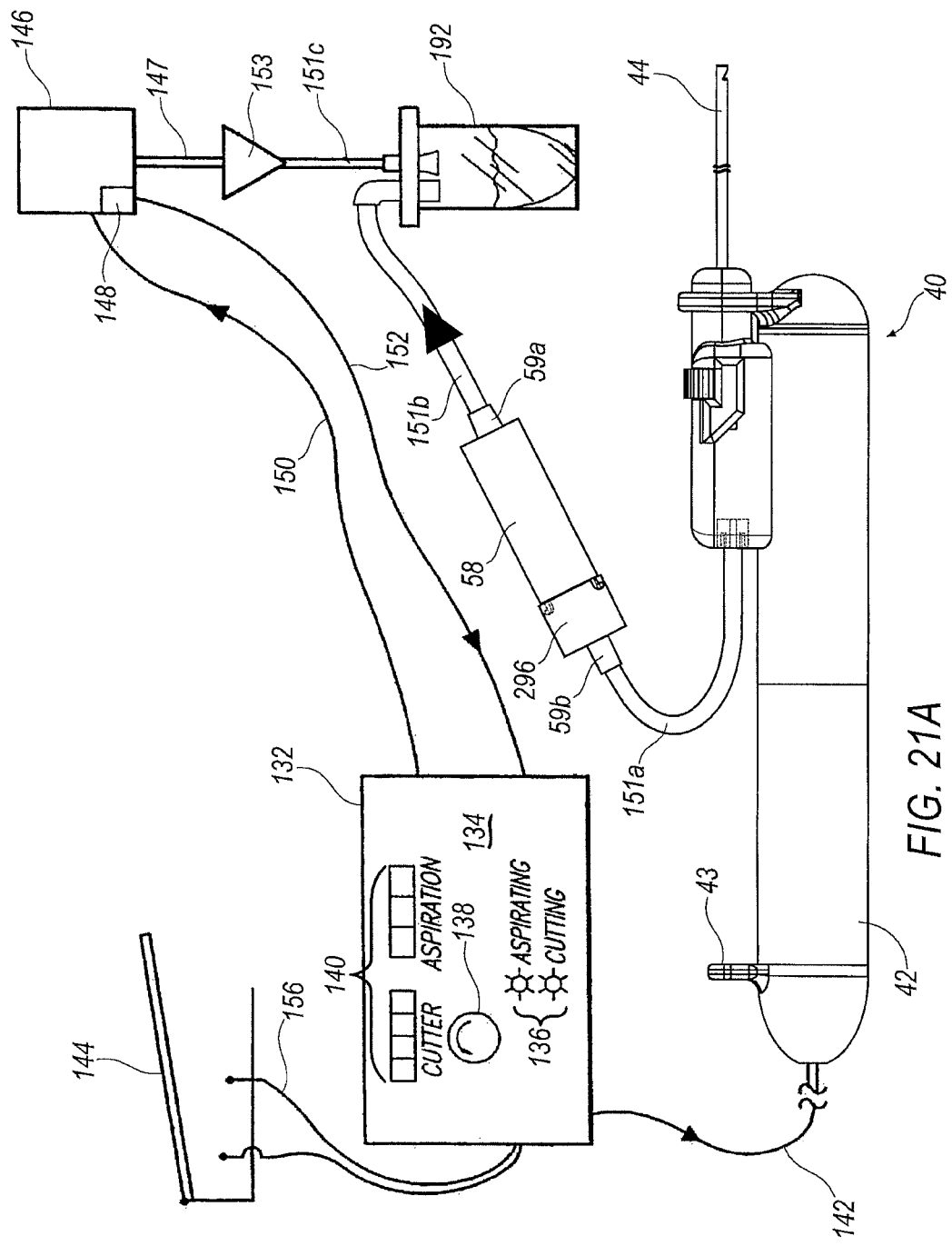
FIG. 21A is a tissue cutting system including a remote tissue collector, control console, foot pedal, and the tissue cutting device of FIG. 1.

As mentioned above, tissue cutting device 40 aspirates tissue samples received in inner cannula lumen 78 to cause the tissue samples to move in the proximal direction along the length of the inner cannula 76. In certain methods of use, device 40 is used to resect tissue without collecting tissue samples for further analysis. In such embodiments, a tissue collector need not be provided. In other embodiments wherein tissue collection is desired, device 40 preferably includes a tissue collector 58 into which aspirated tissue samples are deposited during a tissue cutting procedure. Tissue collector 58 may be located remotely from handpiece 42 and outside the sterile field during a tissue cutting operation as shown in FIG. 21A. However, in an alternative embodiment, as best seen in the examples of FIGS. 1-7, tissue collector 58 is removably connected to handpiece 42. In either embodiment, a fluid collection canister 192 is preferably located between tissue collector 58 and a source of vacuum (such as vacuum generator 153 in FIG. 21A) to protect the vacuum generating apparatus from becoming contaminated or damaged by aspirated fluids. In those embodiments that lack a tissue collector, fluid collection canister 192 may be provided to collect both aspirated fluid and tissue.

Referring to FIGS. 4-7, tissue collector 58 is connected to upper housing 52 proximally of the inner cannula 76 to receive the aspirated tissue samples. Tissue collector 58 is a generally cylindrical, hollow body with an interior volume that is in fluid communication with the inner cannula lumen 78 and a source of vacuum (not shown in FIGS. 4-7). Tissue collector 58 is removably secured to housing connector 96 to allow for the periodic removal of collected tissue samples. Tissue collector 58 is preferably secured to upper housing 52 in a manner that provides a substantially leak-proof vacuum seal to maintain consistent aspiration of severed tissue samples. A vacuum hose fitting 59 is formed on the proximal end of tissue collector 58 and is in fluid communication with the interior of tissue collector 58 and with a vacuum generator, as will be discussed below.

Figure 4:
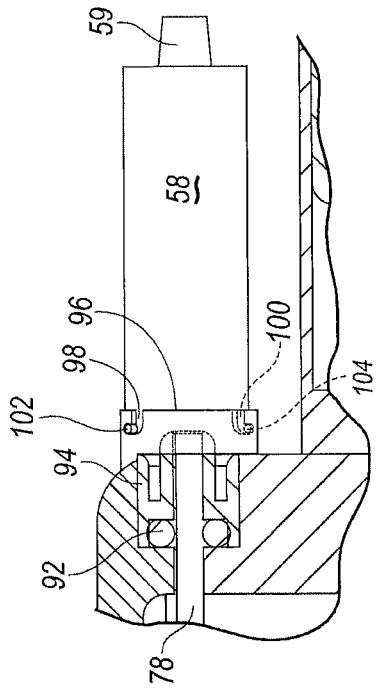
FIG. 4 is a partial cross-sectional view of the tissue cutting device of FIG. 1 in a first configuration in which a device-mounted tissue collector is disconnected from a tissue cutting device housing.
Figure 5:
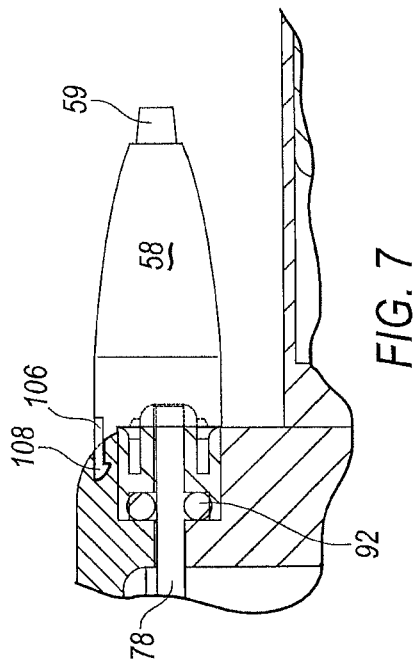
FIG. 5 is a partial cross-sectional view of the tissue cutting device of FIG. 4 in a second configuration in which the device-mounted tissue collector is connected to the tissue cutting device housing.

In the embodiment of FIGS. 4-5, housing connector 96 is a generally cylindrical, flange extending proximally from upper housing 52. Upper shell 54 and lower shell 56 of upper housing 52 cooperatively define a cavity into which a seal holder 94 is partially disposed. Seal holder 94 includes a distal annular recess in which a seal 92, such as an o-ring, is disposed. Seal holder 94 also includes a central lumen through which inner cannula 76 is slidably disposed. A proximally projecting portion 95 of seal holder 94 projects away from upper housing 52 in the proximal direction and is received within housing connector 96. As best seen in FIGS. 2 and 3, inner cannula proximal end 77 preferably remains within seal holder 94 as inner cannula 76 reciprocates during operation of tissue cutting device 40. However, proximal end 77 moves within seal holder 94 as inner cannula 76 reciprocates. Seal 92 preferably comprises a resilient material such as an elastomeric material. The sealing engagement of seal 92 and inner cannula 76 prevents air or fluids from leaking between inner cannula 76 and upper housing 52 and aids in maintaining consistent aspiration of samples through the inner cannula lumen 78.

Housing connector 96 includes connecting features 98 and 100 which are configured to engage with corresponding connecting features 102 and 104 on tissue collector 58. In the embodiment of FIGS. 4 and 5, connecting features 98 and 100 are "J" shaped slots formed in housing connector 96, and connecting features 102 and 104 are complementary protrusions formed on tissue collector 58 which engage connecting features 98 and 100, respectively. To connect tissue collector 58 to housing connector 96, protrusions 102 and 104 are aligned with slots 98 and 100, and tissue collector 58 is then inserted into housing connector 96 in the distal direction. Tissue collector 58 is then rotated to fully engage protrusions 102 and 104 with slots 98 and 100. A seal 103 is provided around the circumference of tissue collector 58 to sealingly engage the inner surface of housing connector 96.

Figure 6:
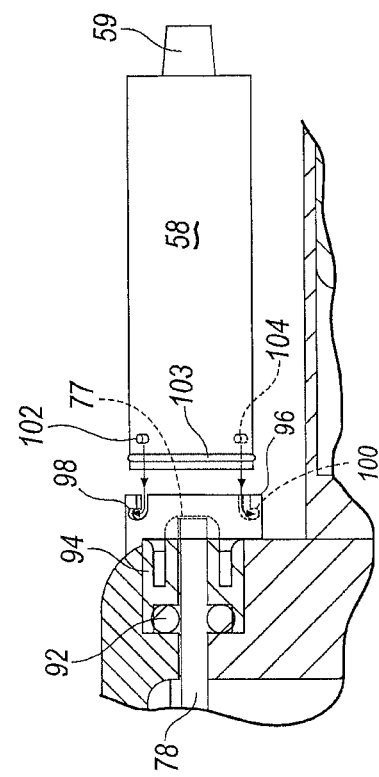
FIG. 6 is a partial cross-sectional view of an alternate embodiment of the tissue cutting device of FIG. 1 in a first configuration in which the device-mounted collector is disconnected from the tissue cutting device.
Figure 7:
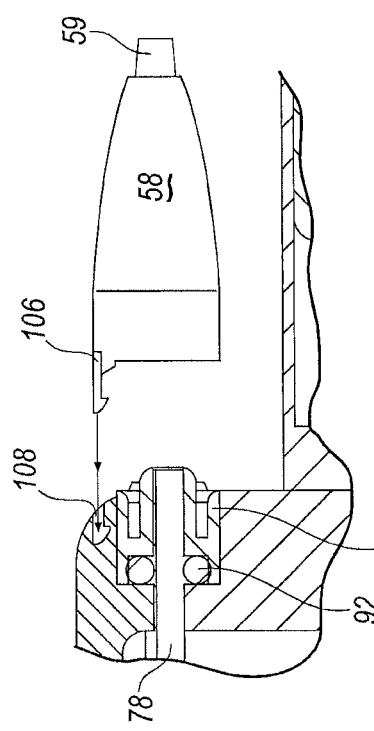
FIG. 7 is a partial cross-sectional view of the tissue cutting device of FIG. 6 in a second configuration in which the device-mounted tissue collector is connected to the tissue cutting device.
Figure 13:
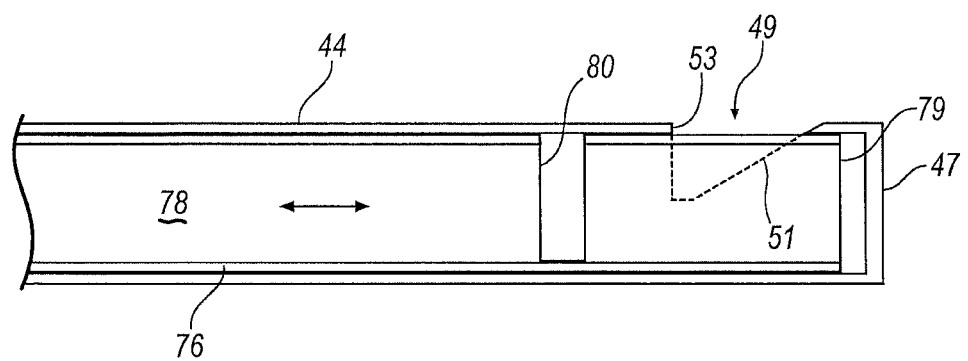
FIG. 13 is a partial cross-sectional view of a distal region of the outer cannula and the inner cannula of the tissue cutting device of FIG. 1, depicting the inner cannula in a first relative position with respect to the outer cannula.

An alternate embodiment of tissue collector 58 is depicted in FIGS. 6 and 7. In the embodiment of FIGS. 6 and 7, tissue collector 58 is semi-elliptical in cross-section and includes a hollow interior for receiving samples, as in the embodiment of FIGS. 4 and 5. In the embodiment of FIGS. 6 and 7, a cylindrical flange housing connector 96 is not provided. Instead, upper housing 52 is formed with an engagement recess 108 that engages a complementary clip 106 formed on tissue collector 58. In each of the foregoing embodiments, tissue collector 58 may be provided with a filter (not shown) in its interior for collecting solid tissue samples while allowing liquids and gases (e.g., air) to pass through. Exemplary filters include medical grade mesh filters with a mesh size smaller than that of tissue snippets 112.

In the embodiments of FIGS. 4-7, tissue collector 58 preferably has a longitudinal axis that is not collinear with the longitudinal axes of handpiece 42, motor 62, or cam 64. The longitudinal axis of tissue collector 58 is preferably substantially coaxial with the longitudinal axis of inner cannula 76 to yield an "in-line" filter configuration. Tissue collector 58 and inner cannula 76 are both spaced apart from and substantially parallel to the longitudinal axes of handpiece 42, motor 62, and cam 64. Thus, the cutting axis (i.e., the outer cannula longitudinal axis) and sample aspiration path axis are not coaxial with the longitudinal axis of the handpiece 42. As a result, when device 40 is used to cut tissue, the surgeon's view of the cutting axis is not obstructed by his or her hand. In addition, the surgeon can treat the proximal end of the filter as a "gun sight" and align it with a tissue sample to be cut to thereby align the outer cannula 44 with the tissue sample, providing enhanced ergonomic benefits over previous devices, in particular, previous neurosurgical devices. In the case of a device with a remote tissue collector 58 such as the one depicted in FIGS. 21A and 21B, the user can treat the proximal end of upper housing 52 as a gun sight and align it with a target tissue.

Figure 18:
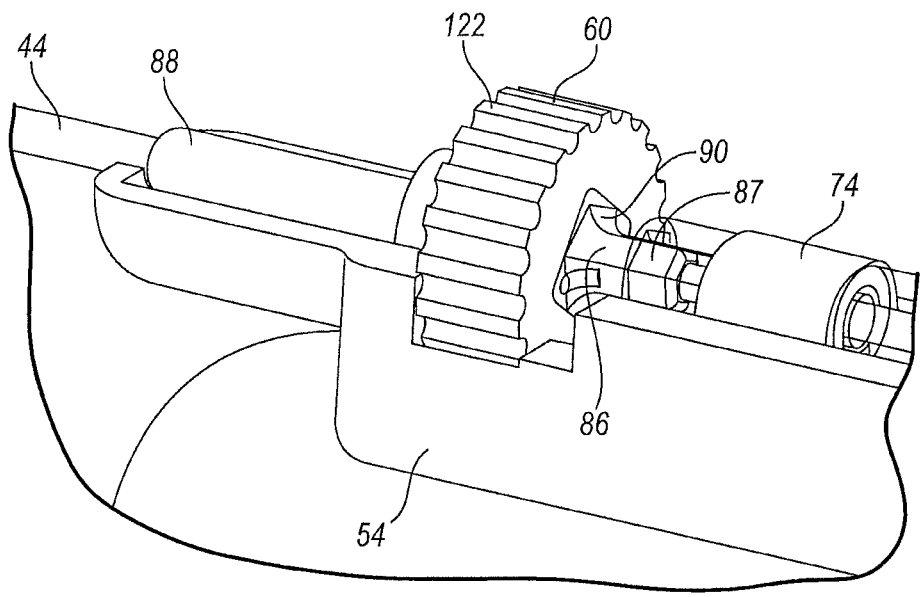
FIG. 18 is a partial perspective view of a portion of the tissue cutting device of FIG. 1 with an upper shell of an outer sleeve upper housing removed to show a dial for rotating an outer cannula.
Figure 19:
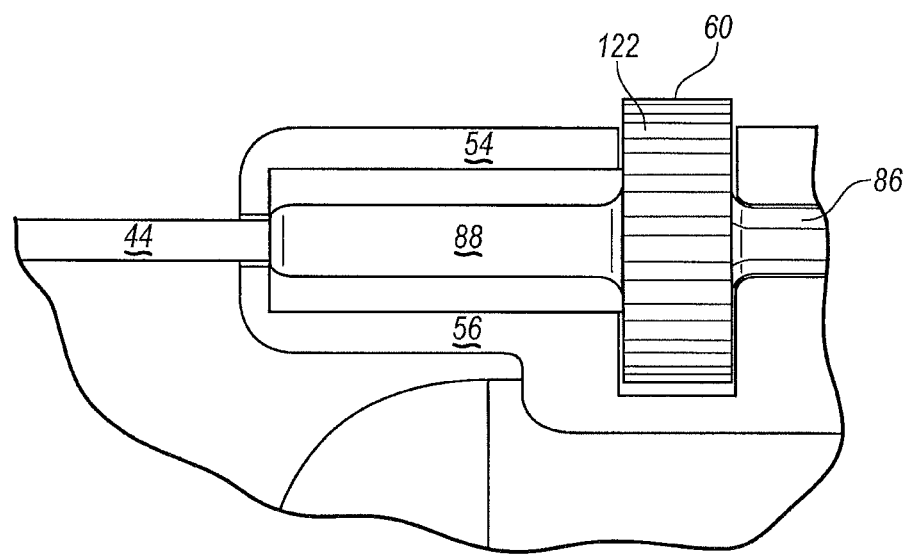
FIG. 19 is a partial side cross-sectional view of the portion of the tissue cutting device of FIG. 18.

When device 40 is used to cut tissue, outer cannula opening 49 must be aligned with the target tissue of interest to receive it for cutting. The entire device 40 can be rotated about the longitudinal axis of handpiece 42 to place outer cannula opening 49 at the desired location. However, this technique can be awkward and may reduce the surgeon's dexterity. Thus, in an exemplary embodiment, device 40 includes a selectively rotatable outer cannula 44. As best seen in FIGS. 18-20, a rotation dial 60 is provided and is rotatably seated in a cavity defined by upper shell 54 and lower shell 56 of upper housing 52. Rotation dial 60 is configured such that when it is rotated, it causes outer cannula 44 to rotate about its longitudinal axis with respect to handpiece 42. Rotation dial 60 is preferably connected to an outer cannula connector portion 88. In the embodiment of FIGS. 18-20, outer cannula connector portion 88 is a sleeve that is integrally formed with rotation dial 60 and which is fixedly secured to outer cannula 44 such as by an adhesive or other known connection means. In the exemplary embodiment of FIG. 20 rotation dial 60 has an outer diameter that is greater than that of sleeve 88. For ease of viewing, fluid supply sleeve 302 is not shown in FIG. 20.

As mentioned previously, inner cannula 76 includes a hinge 80 to allow inner cannula cutting section 83 to pivot toward outer cannula opening 49 when device 40 is in operation. In order to ensure the correct operation of hinge 80, the circumferential alignment of hinge 80 and outer cannula opening 49 should be maintained. Thus, rotation dial 60 is preferably connected to inner cannula 76 such that when rotation dial 60 is rotated, both outer cannula 44 and inner cannula 76 rotate in a fixed angular orientation with respect to one another by an amount that directly corresponds to the amount by which rotation dial 60 is rotated. Rotation dial 60 may be directly connected to inner cannula 76 or may use an intervening connecting device. However, rotation dial 60 should be configured to allow inner cannula 76 to reciprocate with respect to rotation dial 60. As best seen in FIG. 20, rotation dial inner cannula connector 86 may be provided to connect rotation dial 60 to inner cannula 76. Rotation dial inner cannula connector 86 comprises a proximal sleeve 87 disposed about inner cannula 76 and a distal, radially extending annular flange 90 with an outer diameter greater than that of the sleeve 87. Sleeve 87 and flange 90 may be in the shape of circular cylinders. Alternatively, and as shown in FIGS. 18-19, sleeve 87 and flange 90 may be in the shape of polygonal cylinders. Sleeve 87 is slidably received within the annular cavity 130 at the distal end 126 of the cannula transfer 74 and keyed to the inner surface of cannula transfer 74 at annular cavity 130 such that sleeve 87 can reciprocate with respect to cannula transfer 74 while causing cannula transfer 74 to rotate with sleeve 87 when rotation dial 60 is rotated. When inner cannula 76 is reciprocated, cannula transfer distal end 126 reciprocates with respect to sleeve 87, thereby variably adjusting gap "G" defined within annular cavity 130 (FIG. 20). Alternatively, cannula transfer distal end 126 may be slidably received in an annular cavity formed in sleeve 87 and may be keyed to the inner surface of the annular cavity so that cannula transfer may reciprocate with respect to sleeve 87 while still rotating with sleeve 87 when dial 60 is rotates.

As best seen in FIG. 20, rotation dial 60 includes a first annular cavity 61 that is sized to receive and engage flange 90 in a close fitting relationship. Rotation dial 60 may be press fit to flange 90. In addition, adhesive connections or mechanical connections may be used. Because rotation dial 60 is directly or indirectly connected to both outer cannula 44 and inner cannula 76, both cannulas rotate in direct correspondence to the rotation of rotation dial 60, thereby allowing the user to adjust the orientation of outer cannula opening 49 and inner cannula hinge 80 in a circumferential direction with respect to handpiece 42. As a result, surgeons need not rotate the entire tissue cutting device 40 to obtain the desired angular orientation.

Rotation dial 60, outer cannula 44, and inner cannula 76 are preferably configured for 360° rotation. In addition, tactile indicators are preferably provided on rotation dial 60 to allow a user to reliably determine the extent to which dial 60 has been rotated from a given starting point. The tactile indication may comprise surface features defined on or in the exterior surface of rotation dial 60. In one exemplary embodiment, depicted in FIGS. 18-20, a plurality of ridges 122 is provided around the circumference of rotation dial 60 to provide tactile indication. The ridges also act as grips and facilitate the surgeon's ability to rotate the dial 60 without transferring unwanted motion to the surgical site.

As mentioned previously, vacuum (sub-atmospheric pressure) is applied to tissue collector 58 to aspirate severed tissue samples through inner cannula 76 in the proximal direction. The application of vacuum to inner cannula 76 via tissue collector vacuum hose fitting 59 will have a propensity to produce a vacuum at proximal end 45 of outer cannula 44 if leakage occurs between inner cannula 76 and the components of upper housing 52. The generation of a vacuum at outer cannula proximal end 45 will in turn cause fluids and/or tissue samples at the distal end of outer cannula 44 to flow into the annular clearance between inner cannula 76 and outer cannula 44 that extends from its proximal end at outer cannula proximal end 45 to its distal end at inner cannula distal end 79. This fluid and/or tissue can result in blockage of the annular clearance and increased friction between the inner cannula 76 and outer cannula 44, resulting in degraded performance. Accordingly, a seal 129 is preferably provided to prevent air artifacts, fluid (water, saline, blood, etc.) flow, and tissue sample flow in the annular clearance between inner cannula 76 and outer cannula 44. The seal 129 is preferably disposed adjacent the proximal end of the annular clearance between inner cannula 76 and outer cannula 44, i.e., proximally adjacent to outer cannula proximal end 45. As shown in FIG. 20, seal 129 is preferably annular and circumscribes inner cannula 76, extending from the outer surface of inner cannula 76 in a radially outward direction as well as longitudinally along a portion of the length of inner cannula 76.

In the embodiment of FIG. 20, rotation dial 60 and sleeve 87 act as a seal housing and include a seal cavity 131 which is an annular cavity disposed immediately adjacent to and distal of first annular cavity 61. Seal cavity 131 is sized to accept seal 129 therein. The seal 129 may be a conventional seal such as a solid, flexible and/or elastomeric o-ring. However, seal 129 is preferably amorphous and comprises a thixotropic material that is a semi-solid. It is further preferred that seal 129 fill the entirety of seal cavity 131 to ensure that cavity 131 is substantially leak free. In the exemplary embodiment of FIG. 20, seal cavity 131 has an outer diameter that is greater than the outer diameter of outer cannula 44. Moreover, the annular thickness of seal cavity 131 is preferably greater than the annular clearance between outer cannula 44 and inner cannula 76 to better ensure complete sealing of the annular clearance.

In one exemplary embodiment, seal 129 is a grease--such as the so-called "high vacuum greases"--that is formulated to withstand vacuum conditions. Suitable high vacuum greases include halogenated polymers. The halogenated polymers are preferably based on cyclic ether or unsaturated hydrocarbon polymeric precursors. In one exemplary embodiment, a perfluoropolyether (PFPE) grease is used. Examples of such greases include the FOMBLIN® family of greases supplied by Solvay Solexis, Inc. Other examples of such greases include polytetrafluroroethylene greases ("PTFE") such as TEFLON® greases supplied by DuPont. One suitable high vacuum grease is FOMBLIN® Y VAC3 grease, which is a PFPE grease with a PTFE thickener. The semi-solid seal 129 preferably has a kinematic viscosity at 20° C. of at least about 500 cSt, more preferably at least about 800 cSt, and even more preferably at least about 1200 cSt. Semi-solid seal 129 preferably has a kinematic viscosity at 20° C. of no greater than about 2500 cSt, more preferably no greater than about 2000 cSt, and even more preferably no greater than about 1700 cSt.

The use of a semi-solid seal 129 has several advantages. Because the seal is semi-solid, it will tend to absorb and dampen vibrations transmitted from the reciprocation of the inner cannula, thereby reducing overall vibration of device 40, and in particular, the vibration transmitted to outer cannula 44. The dampening of such vibrations is particularly beneficial because it reduces the transmission of unwanted vibrations to outer cannula 44 which can disturb delicate neurosurgical procedures. Moreover, because it is not a solid seal, seal 129 will experience less heating and wear as it is frictionally engaged by the reciprocating inner cannula 76. In certain embodiments, a portion of seal 129 will adhere to the outer surface of inner cannula 76 as it reciprocates producing a zero slip velocity condition at the inner cannula 76 outer surface which may further reduce frictional heating and degradation of seal 129. Because semi-solid seal 129 produces less frictional resistance to the reciprocation of inner cannula 76 as compared to conventional solid seals such as o-rings, it also decreases the required motor power consumption and can facilitate the use of lower torque and lower cost motors, which in turn facilitates making device 40 disposable.

Figure 21B:
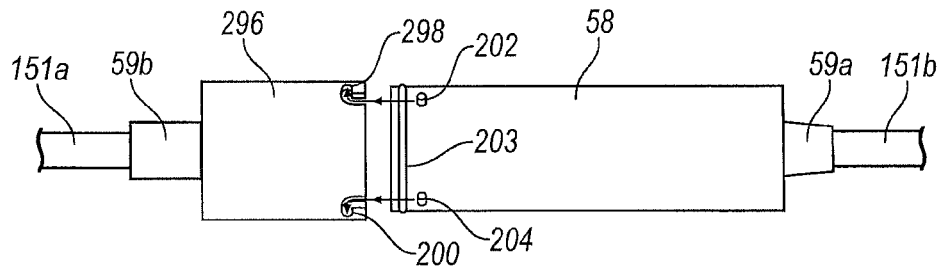
FIG. 21B is an enlarged view of the remote tissue collector of FIG. 21A.

In one configuration, device 40 is connected to a vacuum source and configured for variable aspiration, i.e., configured to supply variable levels of vacuum to inner cannula lumen 78. As depicted in FIG. 21A, in one exemplary implementation, a tissue cutting system is provided which comprises tissue cutting device 40, a tissue collector 58, a controller 132, a vacuum generator 153, a vacuum actuator 144, a controllable valve 146, a vacuum line 151, and a fluid collection canister 192. As mentioned previously, in FIG. 21A tissue collector 58 is located remotely from handpiece 42 and may be placed far enough from the handpiece 42 to either be within the sterile field or be positioned outside of the sterile field during a tissue cutting operation. As best seen in FIG. 21B, tissue collector 58 is generally the same as the tissue collector 58 depicted in FIGS. 4-5. Vacuum line 151a connects the distal end of tissue collector 58 to proximally projecting portion 95 of seal holder 94 on the proximal end of tissue cutting device upper housing 52. In one arrangement, the proximal end of vacuum line 151a includes a hose fitting 59b that is integrally formed with a tissue collector coupler 296. Coupler 296 is similar in structure to tissue collector connector 96 (FIGS. 4-5) and is a cylindrical structure with a hollow interior for receiving a portion of tissue collector 58. As best seen in FIG. 21B, tissue collector 58 includes projections 202 and 204 which engage complementary slots 298 and 200 in coupler 296 in the same manner that projections 102 and 104 engage slots 98 and 100 in FIGS. 4-5. At the proximal end of tissue collector 58, hose fitting 59a engages vacuum line 151b which in turn is connected to fluid collection canister 192. Fluid collection canister 192 is connected to vacuum generator 153 via vacuum line 151c. Vacuum generator 153 is connected to controllable valve 146 by way of pressure line 147.

The outlet of fluid collection canister 192 is preferably substantially liquid free and is connected to vacuum generator 153 via vacuum line 151c. Thus, vacuum generator 153 is in fluid communication with tissue collector 58 and inner cannula lumen 78, thereby generating a vacuum at the proximal end 77 of inner cannula 76 to aspirate severed tissue samples from inner cannula distal end 79 to tissue collector 58. The level of vacuum generated by vacuum generator is preferably variable and selectively controllable by a user. Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

The controllable valve 146 and the vacuum generator 153 provide a means for continuously adjusting and controlling the level of vacuum applied to tissue collector 58 and the proximal end of inner cannula lumen 78. Controllable valve 146 is supplied with a pressurized gas, preferably air, or an inert gas such as nitrogen. In one exemplary embodiment, the pressure applied to controllable valve 146 is about 70 psi.

The system further includes an electrical controller 132 which receives and provides signals to the various components to control or monitor their operations. Controller 132 provides control signals to device 40 via motor drive control line 142 to activate or deactivate motor 62. An aspiration valve control line 150 extends from the controller 132 to the controllable valve 146 which provides pressure to the vacuum generator 153. Signals to the controllable valve 146 through line 150 are used to control the amount of vacuum applied to tissue collector 58.

In one exemplary configuration, controller 132 may receive electrical signals from the various components of the system. For instance, if a closed loop circuit is employed, a pressure transducer 148 associated with the aspiration controllable valve 146, may be configured to send a signal along line 152 to the controller 132. The signal is representative of the pressure supplied through controllable valve 146 to vacuum generator 153. Thus, the transducer 148 may be configured to provide immediate feedback to the controller, which can in turn provide signals to aspiration controllable valve 146. However, it is understood that an open loop circuit may also be employed.

The user can adjust the system operating parameters by using panel controls such as a console knob 138 and/or one or more depressible controllers, such as a foot pedal 144. In one embodiment, foot pedal 144 can be used to activate the motor 62 in device 40, causing the inner cannula 76 to reciprocate within the outer cannula 44. In another embodiment, foot pedal 144 can be used to control the vacuum level supplied from vacuum generator 153 to tissue collector 58 and inner cannula lumen 78. In yet another embodiment, foot pedal 144 can be used both to activate motor 62 and to control the vacuum level supplied from vacuum generator 153 to tissue collector 58. In one arrangement, foot pedal 144 is configured to variably increase the level of vacuum applied to tissue collector 58 from a minimum level to a maximum level as foot pedal 144 is depressed from a first position to a second position. In such an arrangement, the first position is one in which foot pedal 144 is not depressed all or is only slightly depressed, and the second position is one in which foot pedal 144 is fully depressed. In another embodiment, knob 138 is used to set a preselected maximum vacuum level applied by vacuum generator 153. Thus, by depressing foot pedal 144 from a first fully open position to a second fully closed position, a plurality (preferably a continuum) of vacuum levels can be supplied to tissue collector 58 with the maximum vacuum level being user adjustable via knob 138.

In one exemplary embodiment, foot pedal 144 includes two switches (not shown) for providing variable vacuum and activating motor 62. In another exemplary embodiment, once foot pedal 144 is partially depressed from an open or undepressed position, motor 62 is activated. In accordance with the embodiment, continued depression of foot pedal 144 activates vacuum generator 153. Foot pedal 144 preferably provides continuous movement between a fully open and a fully depressed position which in turn corresponds to a plurality, and preferably a continuum, of vacuum levels that are supplied to inner cannula lumen 78. Once foot pedal 144 is fully depressed, the vacuum level supplied to inner cannula lumen 78 corresponds to a previously selected maximum vacuum level.

In certain illustrative examples, the user will adjust the level of vacuum to achieve a desired level of "traction" in the tissue surrounding the tissue to be severed. As used herein, the term "traction" refers to the exertion of a pulling force on tissue surrounding the target tissue to be severed. In some instances, traction may be visualizable by the surgeon with the use of a magnification instrument, such as a microscope or an endoscope. The level of vacuum will also determine the amount of unsevered tissue that is drawn into outer cannula opening 49, and therefore, the size of the severed tissue snippets 112 (FIG. 14). Therefore, when fine shaving operations are desired, the vacuum level will be a relatively lower level than if debulking (large scale tissue removal) is performed. Of course, the pre-selected maximum vacuum level will also affect the maximum size of tissue that is drawn into outer cannula opening 49, and therefore, will affect the maximum size of severed tissue samples during any one operation. Also, the vacuum level may be adjusted based on the elasticity, fibrotic content, and hardness/softness of the tissue.

Console 134 may also include indicator lights 136, one of which indicates the activation of cutting and one of which indicates the activation of aspiration. Console 134 may further include an analog display 140 with readouts for "aspiration" and "cutter." The "aspiration" read out indicates the vacuum level supplied to tissue collector 58 from vacuum generator 153. The "cutter" read out indicates the speed of reciprocation of inner cannula 76. In one embodiment, a speed sensor is mounted in device 40 to determine the speed of reciprocation of inner cannula 76 and the sensor is input to controller 132.

As mentioned previously, when device 40 is used to perform a cutting operation, inner cannula 76 reciprocates within outer cannula opening 49 to sever tissue received within outer cannula opening 49. When a cutting operation is complete, it may be preferred to have inner cannula 76 come to rest at a position that is proximal of the proximal edge 53 of outer cannula opening 49 to ensure that tissue is not trapped between inner cannula distal end 79 and outer cannula cutting edge 51. However, in certain methods of use, tissue cutting device 40 may be used as an aspiration wand without cutting any tissue. In these embodiments, the stop position of the inner cannula distal end 79 within outer cannula opening 49 determines the open area of the outer cannula 44, and therefore, the aspiration levels that can be applied immediately adjacent outer cannula opening 49. Thus, in some preferred embodiments, the inner cannula stop position is user adjustable. Tissue cutting device 40 may be used to aspirate a variety of fluids associated with a neurosurgical procedure, including without limitation blood, saline, cerebrospinal fluid, and lactated ringer's solution. In certain examples, the inner cannula stop position is adjusted to provide a desired degree of aspiration, outer cannula 44 is positioned proximate a target tissue, and vacuum is applied to manipulate the target tissue and draw it into outer cannula opening 49. Outer cannula 44 is then moved to a desired location or orientation, thereby moving the target tissue to the desired location or orientation. Once the target tissue has been satisfactorily manipulated, a cutting operation is initiated. By using device 40 in this manner, target tissues can be drawn away from areas where tissue cutting operations are undesirable, and the cutting can be performed remotely from those areas.

Figure 24:
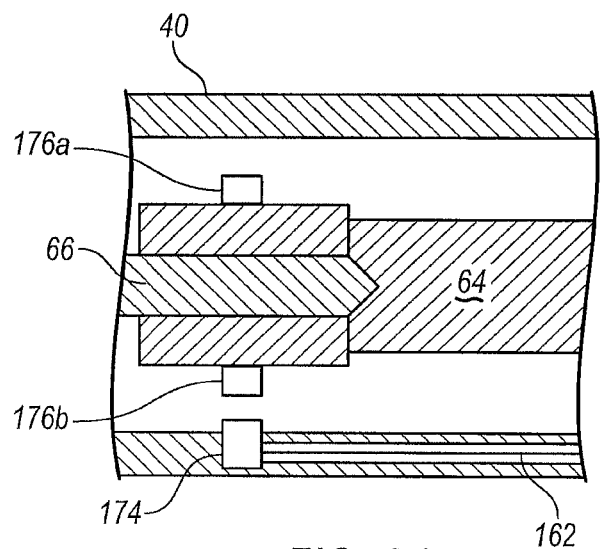
FIG. 24 is a partial cross-sectional view of the tissue cutting device of FIG. 1 depicting motor shaft position sensors for controlling a stop position of an inner cannula.

In one exemplary system, an inner cannula position control is provided which controls the rest position of inner cannula 76 when motor 62 is deactivated. Referring to FIG. 24, cam rotational position indicators 176*a* and 176*b* are mounted on the proximal end of cam 64. In an exemplary embodiment, cam rotational position indicators 176*a* and 176*b* are magnets having opposite poles. A position sensor 174 is mounted on the inner surface of cam housing 69 and generates a signal indicative of the rotational position of indicators 176*a* and 176*b* relative to position sensor 174. As mentioned previously, the rotation of cam 64 correlates directly to the position of inner cannula 76 within outer cannula 44. Thus, the rotation of cam 64 can be sensed to indirectly determine the position of inner cannula 76. Accordingly, indicators 176*a*/176*b* and sensor 174 can be used to determine the position of inner cannula 76 with respect to proximal edge 53 of outer cannula opening 49 (FIGS. 10-12).

Figure 22:
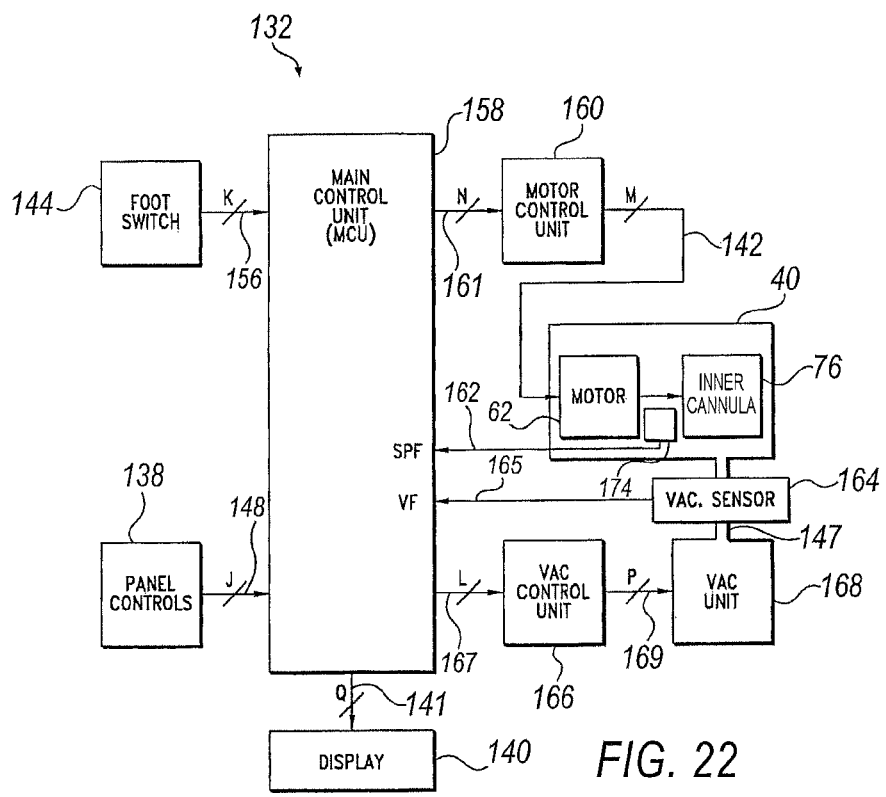
FIG. 22 is a block diagram of a control scheme for the tissue cutting system of FIG. 22.

Referring to FIG. 22, an embodiment of a system for controlling the operation of tissue cutting device 40 is provided. The system includes a main control unit 158 ("MCU"), which (in the embodiment shown) is configured as a microprocessor-based system. In one implementation, MCU 158 is incorporated in controller 132 (FIG. 21A) and is operable to control the various operations of the tissue cutting device 40. Foot switch 144 is electrically connected to a number of inputs of MCU 158 via an equal number, K, of signal paths 156, wherein K may be any integer. Panel controls, such as knob 138, are electrically connected to a number of inputs of MCU 158 via an equal number, J, of signal paths 145, wherein J may be any integer.

Display unit 140 is electrically connected to a number of outputs of MCU 158 via an equal number, Q, of signal paths 141, wherein Q may be any integer. In one exemplary implementation, depicted in FIG. 21A, display unit 140 is provided on console 134.

As mentioned previously, tissue cutting device 40 includes motor 62 coupled to the inner cannula 76 by an inner cannula drive assembly 63. The motor 62 is electrically connected to motor control unit 160 via a number, M, of signal paths 161 wherein M may be any integer. The motor control unit 160 is, in turn, connected to a number of outputs of MCU 158 via an equal number, N, of signal paths 161. Cam rotational position sensor 174 is electrically connected to a motor shaft position feedback input (SPF) of MCU 158 via signal path 162, and provides a motor stop identification signal thereon as will be more fully described hereinafter. The motor shaft stop identification signal provided by sensor 174 on signal path 162 preferably provides MCU 158 with a motor stop identification signal and may optionally provide a cutter speed signal that is proportional to the motor speed for a geared system or identical to the motor speed for a direct drive system.

Tissue cutting device 40 is further mechanically connected to a vacuum unit 168 (e.g., a combination of controllable valve 146 and vacuum generator 153 in FIG. 21A) via conduit 163 (not shown in FIG. 22), whereby the vacuum unit 168 provides a controllable vacuum level to device 40 for aspirating tissue received in inner cannula lumen 78. Vacuum unit 168 is electrically connected to a vacuum control unit 166 via a number, P, of signal paths 169 wherein P may be any integer. The vacuum control unit 166 is, in turn, connected to a number of outputs of MCU 158 via an equal number, L, of signal paths 167, wherein L may be any integer. A vacuum sensor 164, which may be a temperature compensated solid-state pressure sensor, may be positioned within the conduit 151 and electrically connected to a vacuum feedback (VF) input of MCU 158 via signal path 165. Alternatively, the vacuum sensor 164 may be disposed within hand piece 42 or within the vacuum unit 168 itself.

In operation, the MCU 158 is responsive to a vacuum command signal, preferably provided by a corresponding control mechanism associated with control panel 138, foot pedal 144, or an equivalent control mechanism, to provide one or more corresponding vacuum control signals to vacuum control unit 166 along signal paths 167. The vacuum control unit 166, in turn, is responsive to the one or more vacuum control signals to activate the vacuum unit 168 to thereby provide tissue cutting device 40 with a desired level of vacuum. The actual vacuum level provided to tissue cutting device 40 is sensed by vacuum sensor 164, which provides a corresponding vacuum feedback signal to the vacuum feedback input VF of MCU 158. The MCU 158 is then operable to compare the vacuum feedback signal with the vacuum command signal and correspondingly adjust the one or more vacuum control signals to achieve the desired vacuum level within tissue cutting device 40. Such closed-loop feedback techniques are well known in the control systems art.

In one alternative embodiment, the MCU 158 can be replaced by individual microprocessors controlling the input and output for controlling the operation of the motor 62 and the vacuum unit 168. In this alternative embodiment, the motor control and vacuum control microprocessors can be PIC16CXX Series microcontrollers provided by Microchip, Inc. of Chandler Ariz. The motor control microcontrollers can receive input signals from the motor driver 172 (FIG. 23) and position sensor 174, as well as the foot switch 144 and panel controls 138. Likewise, the vacuum microcontroller can receive input signals from the vacuum sensor 164, the foot switch 144 and panel controls 138. Each microcontroller can provide its own output to its driven component and have its own display, such as an LED display, indicative of its operational status. Moreover, the two units can communicate with each other to ensure clean cutting by proper timing of the cutting and aspiration functions.

Figure 23:
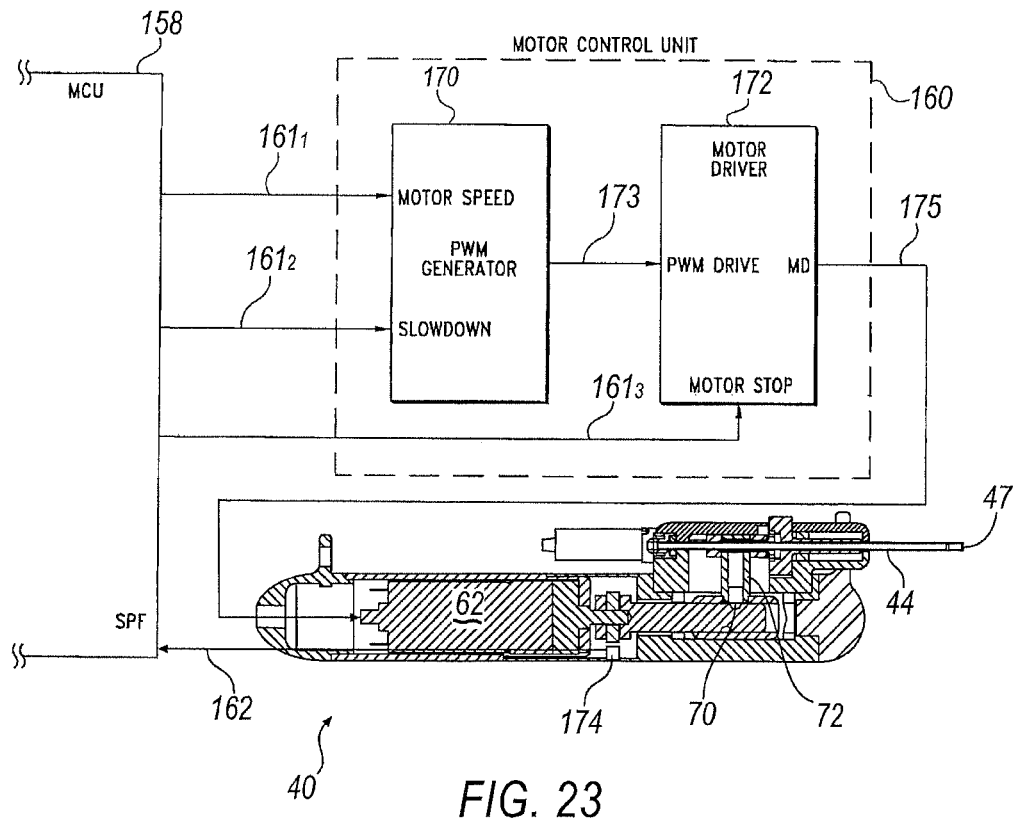
FIG. 23 is diagram of the tissue cutting device of FIG. 1 and the motor control unit of FIG. 22.

Referring now to FIG. 23, one exemplary embodiment of the motor control unit 160 is shown in greater detail. The motor control unit 160 in one embodiment includes a pulse width modulation (PWM) generator circuit 170 having a motor speed input connected to one of the MCU outputs $161_1$. If motor speed control is provided, the output $161_1$ can provide a variable voltage signal indicative of a desired motor speed and based upon the position of a throttle, foot pedal, or other actuator. In certain embodiments, an additional input is connected to another one of the MCU outputs $161_2$. The signal at this output $161_2$ can be a motor slowdown signal as described below. Alternatively, the output $161_2$ can constitute a braking signal used in connection with a current feedback motor controller. As a further alternative, the slowdown command may be communicated via the motor speed command itself, rather than through a separate signal $161_2$. In this instance, the output $161_2$ may not be required.

In the illustrated embodiment, the PWM is disposed within the motor control unit 160. Alternatively, the PWM can be integrated into the MCU 158, or into the separate motor control microprocessor discussed above. In embodiments that include motor speed control, the motor speed input receives a motor speed signal from MCU 158 indicative of desired operational speed of the motor 62. The slowdown input can receive a speed adjustment signal from the MCU 158 based on an actual motor speed signal provided by a motor sensor associated with the motor 62.

A motor driver circuit 172 is electrically connected to PWM generator circuit 170 via signal path 173 and receives a PWM drive signal therefrom, which is a pulse width modulated signal indicative of desired motor speed. The motor driver circuit 172 provides a motor drive signal (MD) to motor 62 via signal path 175. While the disclosed embodiment contemplates digital control of the motor using the PWM generator circuit 170, alternative embodiments can utilize closed loop feedback analog circuits, particularly where slower cutting speeds are contemplated.

The motor drive signal includes a motor stop input that is connected to another one of the MCU outputs $161_1$. In accordance with an aspect of the present disclosure, MCU 158 provides a motor stop signal on signal path $161_3$, based on a motor deactivation command provided by foot switch 144 or panel control 138 and also based on a motor stop identification signal provided by sensor 174, to stop the inner cannula 76 in a desired position, as will be more fully described hereinafter. In certain embodiments, only the motor stop signal is utilized to command the motor to stop at the predetermined position. In these certain embodiments, the motor slowdown signal on path $161_2$ can be eliminated, or the input on path $161_2$ can be used for other control signals to the motor control circuit.

Figure 25:
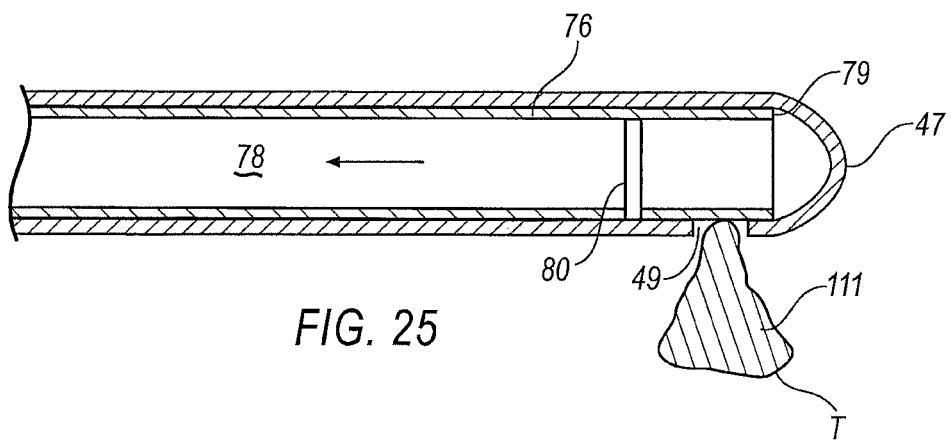
FIG. 25 is a partial cross-sectional view of the outer cannula and inner cannula of the tissue cutting device of FIG. 1 with the inner cannula in a first position relative to the outer cannula.
Figure 26:
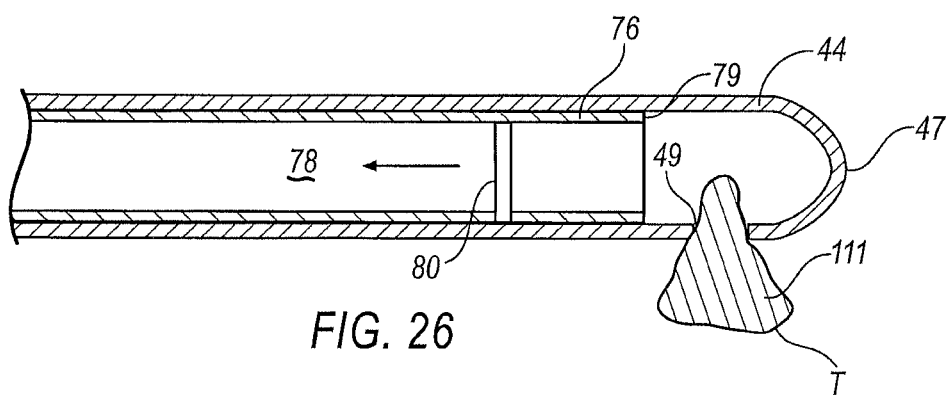
FIG. 26 is a partial cross-sectional view of the outer cannula and inner cannula of the tissue cutting device of FIG. 1 with the inner cannula in a second position relative to the outer cannula.
Figure 27:
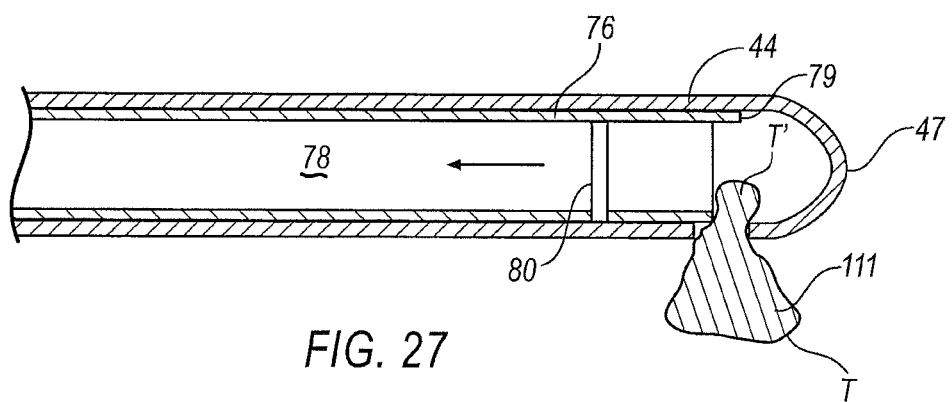
FIG. 27 is a partial cross-sectional view of the outer cannula and the inner cannula of the tissue cutting device of FIG. 1 with the inner cannula in a third position relative to the outer cannula.

As mentioned previously, when tissue cutting device 40 is deactivated, inner cannula 76 may come to rest partially disposed within outer cannula opening 49. Referring to FIGS. 25-27, three different stop positions of inner cannula 76 are shown. For ease of viewing, fluid supply sleeve 302 is not shown. FIG. 27 shows that inner cannula 76 can be stopped in a position in which a portion of the tissue T is trapped between the outer cannula opening 49 and the inner cannula distal end 79. Efforts at withdrawing outer cannula 44 from the surgical site may accordingly result in tearing of the tissue portion T' away from the surrounding tissue base T. Surgeons encountering such trapping would typically be required to re-activate tissue cutting device 40 to release the tissue portion T' from the surrounding tissue base T. To prevent such tissue trapping from occurring, deactivation of the motor 62 is controlled in such a manner that the inner cannula distal end 79 is positioned remotely from the outer cannula opening 49 when inner cannula 76 stops reciprocating. However, in certain methods of use, device 40 is used as an aspiration wand. In those methods, the stop position of inner cannula distal end 79 may be adjusted to different locations within outer cannula opening 49 in order to adjust the level of aspiration supplied to a region of the anatomy proximate outer cannula opening 49. For example, stop positions may be selected that limit the percent open area of outer cannula opening 49 to 25%, 50%, or 75% of the total area of opening 49.

Referring again to FIGS. 23 and 24, controlled deactivation of the motor 62 will now be described in detail. When it is desired to deactivate tissue cutting device 40, a motor stop command is provided such as via foot switch 144 or a panel control 138. In one embodiment, MCU 158 is responsive to the motor stop command to provide a slowdown signal to the PWM generator via signal path $161_2$ which slows the action of motor 62. Preferably, the slowdown signal corresponds to a predefined signal level operable to drive the motor 62 at a motor speed below a motor speed threshold level. Since motor 62 is a brushed DC motor, it has a rotational resistance or resistive torque associated therewith as described above. In addition, in some cases friction between the inner cannula 76 and outer cannula 44 will increase the rotational resistance. Due to this combined rotational resistance, operation of the motor 62 will cease very rapidly or nearly instantly if the motor drive signal on signal path 142 is disabled while driving motor 62 below the motor speed threshold. Accordingly, when device 40 is used to cut tissue, alignment of position indicators 176a or 176b with sensor 174 preferably corresponds to a position of the tissue cutting device 40 at which there is no danger of trapping tissue between inner cannula distal end 79 and the outer cannula opening 49, and sensor 174 is operable to produce the motor stop identification signal when so aligned with indicator 176a or 176b.

In one embodiment, MCU 158 is operable to produce a motor stop signal on signal path $161_3$ when sensor 174 detects alignment of position indicators 176a or 176b therewith after one passage thereby of indicator 176a or 176b since producing the slowdown signal on signal path $161_2$. Allowing one passage of indicator 176a or 176b by sensor 174 after issuing the slowdown signal ensures that the rotational speed of motor 62 is at or below the motor speed threshold when subsequently issuing the motor stop command, regardless of the position of indicator 176a or 176b relative to sensor 174 when the slowdown command was issued. After one passage of indicator 176a or 176b by sensor 174 since issuing the slowdown signal, MCU 158 is responsive to the signal provided by sensor 174 indicative of alignment of indicator 176a or 176b therewith, to produce the motor stop signal on signal path 161$_3$. The motor driver 172 is responsive to the motor stop signal to produce a motor disable signal on signal path 175. Due to the inherent rotational resistance, motor 62 is responsive to the motor disable signal to immediately cease operation thereof with indicator 176a or 176b substantially aligned with sensor 174, and with the inner cannula 76 accordingly positioned so as not to trap tissue between inner cannula distal end 79 and the outer cannula opening 44.

As mentioned above, in one exemplary embodiment, the inner cannula stop position is user adjustable, such as by adjusting a panel control 138 on console 134. In accordance with the embodiment, it is contemplated that the stopped rotational position of cam 64, and therefore the inner cannula distal end 79, may be instead aligned with a predetermined differential distance between the indicator 176a/176b and the sensor 174. The braking characteristics of the inner cannula 76 and motor 62 can be ascertained and the stopping distance determined so that this predetermined differential distance can be calibrated accordingly. However, in a preferred embodiment, when inner cannula 76 comes to rest, the distal end 79 is located proximally of the outer cannula opening 44 by a predetermined distance, as shown in FIG. 26.

A method of using device 40 to perform a tissue cutting procedure will now be described in the context of a neurosurgical procedure involving the cutting of a neurological target tissue. In one example, the target tissue is brain tissue, and in another example the target tissue is spinal tissue, for example, the tissue of an intervertebral disk. In certain exemplary methods, the tissue specimen being cut is a tumor or a lesion.

In accordance with the method, it is first determined whether the cutting operation will be a debulking operation, a fine shaving operation, or a cutting operation that is somewhere in between a debulking and fine shaving operation. A surgical access path is then created to the tissue sample of interest. In one embodiment, the surgical path is created and/or the target tissue is accessed using an "open" procedure in which the target tissue is open to the atmosphere (e.g., a full open craniotomy). In another embodiment, the surgical path is created and/or the target tissue is accessed using a "closed" procedure in which the target tissue is sealed from the atmosphere.

At this point, the distal end 79 of inner cannula 76 is located proximally of outer cannula opening 49 due to the use of an inner cannula stop position control of the type described previously. The maximum vacuum level to be applied to device 40 is then set using panel controls 138. Generally, higher vacuum levels will be used for debulking procedures than for fine shaving procedures as higher vacuum levels will tend to draw relatively larger sections of tissue into outer cannula opening 49. In one embodiment, the panel control 138 is a knob on console 134 that is rotated to set the desired maximum vacuum level.

In one arrangement, device 40 is configured to be gripped with a single hand during a tissue cutting procedure. Thus, the surgeon will grasp handpiece 42 in the fingers of one hand and insert outer cannula 44 to a location proximate the target tissue. Depending on the hand and the surgeon's orientation with respect to the target tissue, the surgeon may then rotate dial 60 to rotate outer cannula 44 about its own longitudinal axis and orient outer cannula opening 49 immediately adjacent the target tissue. The rotation of outer cannula 44 with dial 60 causes inner cannula 76 to rotate such that a fixed rotational or angular relationship is maintained between inner cannula 76 and outer cannula 44. Once the opening is in the desired orientation, the motor 62 is activated, for example, by beginning to depress pedal 144 from its fully undepressed (open) position to a second partially depressed position which causes motor control unit 160 to send a signal to motor 62 on signal path 142. Motor 62 may also be activated by a panel control 138. The rotation of motor 62 causes cam 64 to rotate, resulting in the reciprocation of cam follower 68 and cam transfer 72. The reciprocation of cam transfer 72 causes cannula transfer 74 to reciprocate, thereby reciprocating inner cannula 76 within outer cannula lumen 110.

Once motor 62 is activated, vacuum is supplied to inner cannula lumen 78. In one embodiment, as the pedal 144 is further depressed (beyond the position at which motor 62 is activated), vacuum generator 153 is activated. The surgeon then adjusts the degree of depression of the foot pedal 144 to obtain the desired level of vacuum by visualizing the movement of the target tissue relative to the outer cannula opening 49. In certain embodiments, the surgeon controls the vacuum level to obtain a desired amount of traction in the tissue surrounding the target tissue. If the surgeon desires to apply the previously set maximum vacuum level, he or she depresses pedal 144 to its fully depressed position.

If desired, the surgeon may depress and partially release the pedal 144 a number of times to manipulate the target tissue in a satisfactory manner. Vacuum controller 166 is manipulable to adjust the setpoint of vacuum generator 153 which is manipulable to adjust the inner cannula vacuum level along a continuum of levels below the pre-selected maximum level. In one embodiment, the extent of depression of foot pedal 144 dictates the vacuum set point supplied to vacuum control unit 166 on signal path 167, and therefore, the amount of vacuum provided by vacuum unit 168. Vacuum sensor 164 measures the vacuum supplied to tissue collector 58 and feeds a signal back to main control unit 158 on signal path 165. The measured vacuum is then compared to the set point applied to vacuum control unit 166 via foot pedal 144, and the signal transmitted to vacuum generator 153 is then adjusted to move the measured vacuum value towards the set point. To obtain a vacuum level equal to the maximum pre-set level, pedal 144 is completely depressed. Maximum vacuum levels of at least about 0 in Hg. are preferred, and maximum vacuum levels of at least about 1 in Hg. are more preferred. Maximum vacuum levels of at least about 5 in Hg. are even more preferred, and maximum vacuum levels of at least about 10 in Hg. are still more preferred. Maximum vacuum levels of at least about 20 in. Hg. are yet more preferred, and vacuum levels of at least about 29 in. Hg. are most preferred.

Due to the resistance of the tissue drawn into outer cannula opening 49, cutting section 83 pivots about hinge 80 and toward outer cannula opening 49 as inner cannula 76 travels in the distal direction. The inner cannula cutting section 83 continues to pivot as it travels in the distal direction, eventually compressing tissue within outer cannula opening 49 and severing it. The severed tissue forms a continuum of tissue snippets 112 (FIG. 14) within inner cannula lumen 78. Due to the vacuum applied to tissue collector 58, snippets 112 are aspirated through inner cannula lumen 78 in the proximal direction. They eventually exit inner cannula lumen 78 at inner cannula proximal end 77 and enter tissue collector 58 (or fluid collection canister 192 if no collector 58 is provided). Any fluids that are aspirated exit tissue collector 58 and are trapped in fluid collection canister 192. The surgeon preferably severs tissue at a cutting rate of at least about 1,000 cuts/minute. Cutting rates of at least about 1,200 cuts/minute are more preferred, and cutting rates of at least about 1,500 cuts/minute are even more preferred. Cutting rates of less than about 2,500 cuts/minute are preferred. Cutting rates of less than about 2,000 are more preferred, and cutting rates of less than about 1,800 cuts/minute are even more preferred.

The surgeon may move device 40 around the target tissue until the desired degree of cutting has been completed. Motor 62 is then deactivated, for example, by completely releasing pedal 144 so it returns to its fully undepressed (open) position. If an inner cannula stop position control is provided, inner cannula 76 preferably comes to rest proximally of outer cannula opening 49, as shown in FIG. 26. Outer cannula 44 is then removed from the surgical site. Tissue collector 58 is then removed from upper housing 52 of handpiece 42, and the collected tissue samples are either discarded or saved for subsequent analysis. Fluids collected in canister 192 are preferably discarded. If the remote tissue collector of FIG. 21A is used, tissue samples may be removed from it without removing outer cannula 44 from the surgical site or otherwise disturbing the surrounding tissue.

As mentioned previously, tissue cutting device 40 includes a delivery sleeve 302 which is selectively disposable about outer cannula 44 (i.e., the user can install or remove delivery sleeve 302 from outer cannula 44). As best seen in FIGS. 28-31, delivery sleeve 302 includes an elongated channel section 304 that comprises an outer cannula channel 314 and at least one delivery channel through which fluids or devices may pass. In the depicted embodiment, the at least one delivery channel is a fluid or device delivery channel 312. When the delivery sleeve 302 is in an uninstalled condition (e.g., FIG. 28), the delivery channel 312 may be separate from the outer cannula channel 314 along all or a portion of the length of elongated channel section 304 by a barrier wall, membrane, etc. However, in the example of FIG. 30, the outer cannula channel 314 is in fluid communication with the fluid supply channel 312 along the entire length of elongated channel section 304 when the delivery sleeve 302 is in an uninstalled condition. As best seen in FIG. 30, when delivery sleeve 302 is in an installed condition, outer cannula 44 occupies outer cannula channel 314 and effectively separates outer cannula channel 314 from delivery channel 312.

Referring to FIG. 1, hub 306 is connected to a fluid supply line 308, which is preferably a length of flexible, plastic tubing. Fluid supply line 308 includes a fluid source connector 310 on its proximal end. Fluid source connector 310 may be any known type of connector suitable for providing fluid flow. In the embodiment of FIG. 1, fluid source connector 310 is a male luer fitting.

Hub 306 may be connected to elongated channel section 304 in a variety of ways. One example is depicted in FIG. 29. As shown in the figure, proximal end 317 of elongated channel section 304 is connected to and disposed in the interior of hub 306. Hub 306 preferably includes a complementary channel (not separately shown) in which proximal end 317 of elongated channel section 304 is interfitted. The connection between elongated channel section 304 and hub 306 may be made in a variety of ways, including with adhesives and mechanical fasteners. In addition, elongated channel section 304 may be integrally formed with hub 306 such as by integrally molding elongated channel section 304 and hub 306 as a single piece. In the embodiment of FIG. 29, elongated channel section 304 and hub 306 are separately formed and then connected with an adhesive.

In one exemplary configuration, hub 306 is generally cylindrical in shape. Hub 306 also includes a proximal opening 322 and a distal opening 323. Outer cannula 344 slidably projects through proximal end opening 322 and distal end opening 323. However, at distal hub end opening 323, outer cannula 44 projects through elongated channel section 304 of delivery sleeve 302. As shown in FIG. 1, in one exemplary configuration, the distal end 47 of outer cannula 44 projects through and away from the distal end 320 of elongated channel section 340 when delivery sleeve 302 is in an installed condition on outer cannula 44. An interior channel (not separately shown) is formed in the interior of hub 306 to retain outer cannula 44. Hub 306 may also include exterior surface features which enhance the user's ability to grip the hub such as when delivery sleeve 302 is being slid along outer cannula 44 to reposition delivery sleeve 302 along the length of outer cannula 44 or to rotationally orient the sleeve so that the distal end of the delivery sleeve may be aligned as desired by the user. In one example, a plurality of longitudinally oriented grooves are spaced apart from one another around the circumference of hub 306 and are provided to facilitate gripping. In another example, a plurality of protruding axially oriented ridges are provided and are spaced apart around the circumference of hub 306.

Fluid supply port 316 is provided along the length of hub 306 and is connected to fluid supply line 308. Fluid supply port 316 may comprise an opening in hub 306 and may also include a projecting connector or flange for securing fluid supply line 308 therein. Interior delivery channel 318 is provided in hub 306 and is in fluid communication with supply port 316 and with delivery channel 312 via open proximal end 319 in delivery channel 312. Elongated channel section 304 includes a distal end opening 313 in the delivery channel 312 through fluid which may be provided to the surgical site, typically at or proximate to a target tissue being resected.

Elongated channel section 304 is preferably rigid or semi-rigid and made of a material that is suitable for use with sterilization techniques, such as ethylene oxide sterilization, Sterrad, autoclaving and gamma radiation sterilization. These include resins and metals. One type of suitable polymer material is heat shrinkable tubing. Additional suitable classes of polymers for forming elongated channel section 304 include gamma-compatible polyimides and polyamides, such as Kapton® polyimides supplied by DuPont, and Nomex polyamides supplied by DuPont. Polyester and polyethylene heat shrink tubing are also suitable classes of polymer materials. One exemplary class of heat shrink tubing is polyethylene terephthalate (PET) heat shrink tubing supplied by Advanced Polymers, Inc. Suitable materials for forming hub 306 include stainless steel, aluminum, and polymeric materials such as silicone polymers, and natural or synthetic rubbers.

As shown in FIG. 30, outer cannula channel 314 is partially-cylindrical and defines a partially circular cross-section. Delivery channel 312 may also be partially-cylindrical. However, in the example of FIG. 30, delivery channel 312 is generally in the shape of a partial elliptic cylinder (i.e., a cylinder with a partial elliptical cross-section). Inwardly directed ridges 324 and 326 define a transition between outer cannula channel 314 and fluid supply channel 312 along the length of fluid supply sleeve 302.

As mentioned previously, in one example, elongated channel section 304 is formed from heat shrink tubing. In certain embodiments, the heat shrink tubing is provided as a cylindrical length of tubing and is then modified to provide a dual channel structure such as the one depicted in FIG. 30. The dual channel structure may be provided by disposing the cylindrical heat shrink tubing around a mandrel having the cross-section of elongated channel section 304 which is depicted in FIG. 30 and applying heat to shrink the cylindrical tubing and conform its cross-section to that of FIG. 30.

In one example, when delivery sleeve 302 is in an installed condition on outer cannula 44, outer cannula 44 may be rotated with respect to delivery sleeve 302. In one illustrative example, the surgeon may grip hub 306 with the fingers of one hand to restrain its rotational movement and rotate outer cannula rotation dial 60 with the thumb and/or fingers of the other hand to adjust the circumferential position of outer cannula opening 49. While delivery sleeve 302 may be configured to rotate with outer cannula 44, in many instances it is preferable to maintain the circumferential orientation of fluid supply sleeve 302 in order to prevent delivery supply line 308 from twisting. As shown in FIG. 1, in one preferred orientation, delivery sleeve 302 is circumferentially oriented such that delivery channel 312 is disposed between the longitudinal axis $L_1$ of handpiece lower housing 50 and outer cannula channel 314 in a direction that is substantially perpendicular to handpiece lower housing longitudinal axis $L_1$. In one example, wherein delivery sleeve 302 is used to deliver a hemostatic agent, it is preferable to orient fluid supply channel 312 such that it is spaced apart from outer cannula opening 49 in a direction perpendicular to the lower housing longitudinal axis $L_1$ (see FIG. 31) to prevent the aspiration of the hemostatic agent through outer cannula opening 49. However, other delivery channel 312 orientations may be used depending on the procedure involved and the type of material or device to be delivered.

Delivery sleeve 302 may be connected to a fluid source via delivery supply connector 310. The fluid source may be pressurized or unpressurized. Unpressurized fluids may be elevated to provide the necessary hydrostatic head to deliver the fluids through fluid supply channel 312. Referring now of FIGS. 33-38, an alternative embodiment of a delivery sleeve 402 will now be described. As shown in FIG. 33, delivery sleeve 402 is selectively disposed about outer cannula 44 (i.e., the user can install or remove delivery sleeve 402 from outer cannula 44) to selectively deliver fluid (such as, for example, a hemostatic agent) to the surgical area. Delivery sleeve 402 includes an elongated channel section 404 that comprises an outer cannula lumen 414 and at least one fluid delivery lumen 412. Fluid delivery lumen 412 is connected to the outer cannula lumen 414, at least partially, along their respective lengths. In one exemplary arrangement, fluid delivery lumen 412 and outer cannula lumen 414 are arranged so as to be oriented in a co-planar manner as seen in FIG. 34.

Delivery sleeve 402 is defined by a distal end 420. Further, outer cannula lumen 414 is also defined by a distal end 415 and a proximal end 417 (best seen in FIGS. 35 and 36). Fluid delivery lumen 412 is also defined by a distal end 413 and a proximal end 419 (best seen in FIGS. 35 and 36). As may be seen in FIGS. 33-34, in one exemplary embodiment, distal end 413 of fluid delivery lumen 412 may be slightly angled. For example, as shown in FIG. 34, distal end 413 is angled upwardly toward outer cannula lumen 414. In another exemplary embodiment, distal end 413' of fluid delivery lumen 412 is not angled with respect to distal end 415 of outer cannula lumen 414, as seen in FIG. 40, for example.

A proximal end of the delivery sleeve 402 is positioned in and supported by a hub 406. Details of the hub 406 may be seen in FIGS. 35-38, although it should be noted that for ease of explanation, only a lower section of hub 406 is illustrated. Hub 406 is defined by a body portion 403 that includes a distal face 405 and a proximal face 407. In one configuration, body portion 403 may be formed as mirror image lower and upper sections (lower section visible in FIGS. 34-38) that are configured to snap together or are otherwise connected together to form body portion 403. Body portion 403 includes a first channel 409 and a second channel 411. First channel 409 extends from distal face 405 to a first portion 407a of proximal face 407. First and second channels 409, 411 are configured to receive the proximal end of delivery sleeve 402, as best seen in FIGS. 35 and 36. In one exemplary configuration, proximal ends 417 and 419 are fixedly secured within first and second channels 409, 411 such that delivery sleeve 402 is integrally connected to body portion 406. Proximal ends 417 and 419 may be fixed to body portion 406 in any suitable member. For example, proximal ends 417 and 419 may be glued within first and second channels 409, 411.

In one embodiment, first portion 407a of proximal face 407 includes a mounting portion 410 that is configured to selectively receive a distal end face 59 of upper housing 52 of tissue cutting device 40. A mounting flange 421 may also be provided for selectively receiving a mounting ring 422 disposed about a portion of upper housing 52. Further, body portion 403 may also include a proximally extending clip member 423. As may be seen in FIG. 33, clip member 423 is configured to extend around grasp a portion of mounting ring 422 to provide a quick connect/release mechanism to secure hub 406 to tissue cutting device 40. However, it is understood that other mechanisms for selective attachment of hub 406 to tissue cutting device 40 are also contemplated.

In one embodiment, second portion 407b of proximal face 407 may be configured with a connecting portion 425 that is in communication with second channel 411. In one exemplary arrangement, connecting portion 425 comprises a distal portion 427 and a proximal portion 429. Second channel 411 opens into distal portion 427, while proximal portion 429 opens into second portion 407b of proximal face 407. In one configuration, connection portion 425 is configured with an annular retaining lip 431 that extends at least partially between distal and proximal portions 427, 429. In yet another exemplary configuration, annular retaining lip 431 extends continuously around the inner surface of connecting portion 425. In one exemplary arrangement, connecting portion 425 is configured to be connected to a valve member 435 to which suitable tubing 437 for delivering fluid is attached, as shown in FIG. 39. Valve member 435 may be selectively mounted to the connecting portion 425. Alternatively, valve member 435 may be pre-assembled with hub 406.

Valve member 435 may also be provided with an on/off switch 439 to selectively close a fluid line within valve member 435 (and therefore prevent fluid from flowing through second channel 411 and into fluid lumen 412). In one exemplary arrangement, on/off switch is configured to be finger operable.

Body portion 406 may also be provided with retaining fingers 433. As seen in FIG. 33, when hub 403 is installed on tissue cutting device 40, retaining fingers 433 are disposed on either above or below a portion of tissue cutting device 40, along each side of tissue cutting device 40. When installed, fingers 433 serve to frictionally engage either tissue cutting device 40 or, if provided, mounting ring 422 so as to rotationally fix hub 403 with tissue cutting device 40. In other words, fingers 433 prevent hub 403 from rotating.

A variety of different fluids may be delivered to a target tissue or proximate to the target tissue. In one example, irrigants such as saline are used to flush and subsequently clear excised tissue and body fluids at the surgical site. Saline, when elevated in temperature, may also function as a hemostatic agent to facilitate a "clotting cascade" which ultimately leads to the clotting of severed blood vessels in tumors or other tissues at the surgical site. Other hemostatic agents, sealants, and/or tissue adhesives may also be delivered to a surgical site via fluid supply channel 312. Examples include liquid embolic systems such as Neucrylate, a cyanoacrylate monomer derivative supplied by Valor Medical. Neurcrylate is delivered as a liquid and forms a spongy, solid material upon contacting blood. Another example of a suitable hemostatic agent is supplied by Medafor, Inc. under the name Arista AH Absorbable Hemostat. Arista AH functions as a molecular filter by separating serum from cellular constituents. It absorbs water from the blood and forms a gel matrix that slows blood flow and serves to enhance clotting.

Fibrin sealants may also be delivered to a surgical site via delivery channel 312 or fluid delivery lumen 412. One suitable hemostatic matrix sealant is FloSeal®, a fibrin sealant comprising human thrombin which is supplied by Baxter Hyland Immuno. Another suitable sealant is Tisseel, a VH Fibrin Sealant comprising human thrombin, human fibrinogen, and bovine aprotinin. Certain sealants may comprise two or more fluid components that are mixed at or near the site of delivery. In such cases, the at least one fluid supply channel 312 and/or fluid lumen 412 preferably comprises two or more fluid supply channels that contain the respective two or more fluid components which are mixed at open distal end 313 of fluid supply channel 312 or distal end 413 of fluid lumen 412. Synthetic sealing agents may also be delivered via delivery channel 312 and/or fluid lumen 412. One such example is CoSeal, a hydrogel comprising 2 polyethylene glycol polymers supplied by Baxter. The 2 polymers are preferably delivered via two separate fluid delivery channels and chemically bond to one another on mixing to form a mechanical barrier that slows bleeding. Another suitable synthetic seal is Duraseal, which is supplied by Confluent Surgical. Duraseal comprises a polyethylene glycol polymer ester solution that is mixed at the point of delivery with a trilysine amine solution. Thus, delivery sleeve 302 and/or delivery sleeve 402 is preferably provided with two fluid delivery channels to facilitate mixing of the two solutions at the point of delivery.

As mentioned above, in certain examples, it may be desirable to include two or more delivery channels in delivery sleeve 302 and/or 402. However, the two or more delivery channels need not be entirely separate along the length of sleeve 302 and/or 402. Instead, they may combine to form a single channel mixing zone at a defined distance from distal end opening 313/413. The length of such a mixing zone is preferably selected to ensure thorough mixing without allowing the fluids to form a solidified mixture prior to discharge from delivery sleeve 302/402.

Tissue adhesive glues are another category of fluids that may be delivered via delivery sleeve 302/402. Suitable tissue adhesive glues include those formed from formaldehyde or glutaraldehyde-based tissue adhesive glues. One suitable type of glutaraldehye based tissue adhesive glue is BioGlue® a protein hydrogel comprising bovine serum albumin, glutaraldehyde, and water which is supplied by Cryolife, Inc.

In certain examples, elongated channel section 304/404 is formed with an imageable material to facilitate the identification of its position within the patient. In one example, elongated channel section 304/404 includes an MRI-imageable material. In another example, elongated channel section 304/404 includes a positron emission tomography (PET) imageable material such as a radioactive isotope. Suitable isotopes include halogenated sugars such as [$^{18}$F]fluorodeoxyglucose and isotopes of amino acids such as [$^{11}$C] methionine. In one example, PET imaging is performed while fluid supply sleeve 302/402 is inserted in the patient to locate the position of fluid supply sleeve 302/402 (and outer cannula 44) within the patient and relative to certain anatomical structures. The radioactive isotope may be incorporated in the elongated channel section 304/404 in a number of ways. In one example, the radioactive isotope is added to a molten resin used to form elongated channel section 304/404 and suspended within the solidified resin. In another example, elongated channel section 304/404 is formed with bores (holes, cavities, channels) and dipped into a solution containing the radioactive isotope. The isotope then wicks into the bores same as above. It could also have a "rough" surface which would allow the radioactive material to remain in the valleys of the surface, it could also have a charged surface that would allow the radioactive material/solution to be attracted to and stay on the elongated tube, etc.

Delivery sleeve 302/402 can be used to deliver fluids when tissue cutting device 40 is used in a tissue cutting mode or in an aspiration wand mode. In one example, a tissue removal system comprising tissue cutting device 40 with delivery sleeve 302/402 installed on the outer cannula 44 is provided. A fluid source is provided and is connected to delivery connector 310 and/or valve member 435. A valve may be provided between the fluid source and delivery connector 310 to allow the surgeon to selectively deliver the fluid to delivery sleeve 302. Alternatively, a valve may be provided between fluid source connector 310 and hub 306.

In yet another embodiment, delivery sleeve 302/402, and more particularly fluid delivery channel 312 or fluid cannula 412, may be used to provide selective aspiration. For example, in certain circumstances, such as with fluid filled abnormalities such as cysts, abscesses, etc., it may be desirable to aspirate to a separate collection container than the tissue collection chamber of the tissue cutting device 40.

For the embodiment shown in FIGS. 1 and 28-32, the surgeon selectively positions delivery sleeve 302 at a desired location along the length of outer cannula 44. In one example, the surgeon grips hub 306 and advances or retracts fluid supply sleeve 302 along outer cannula 44 to the desired location. The outer cannula 44 is then inserted into the patient's body to a location proximate the target tissue. In the embodiment shown in FIGS. 33-40, hub 406 is slid onto outer cannula 44 until distal end face 59 of upper housing 52 is seated within mounting portion 410 of first portion 407a. Clip member 423 (or other suitable retaining member) is then selectively attached to tissue cutting device 40. Further, valve member 435 (and tubing 437) are mounted to connecting portion 425 of second portion 407b.

Once hubs 306/406 are fluidly connected to the fluid sources, fluid is supplied from the fluid source through delivery supply line 308 (or tubing 437), into hub 306/406, and through delivery supply channel 312 and fluid lumen 412. The fluid then exits delivery sleeve 302/402 at delivery channel open distal ends 313/413 and contacts the target tissue and/or surrounding tissues proximate the target tissue. A vacuum level may then be supplied to inner cannula lumen 78 in the manner described previously. Motor 62 may be activated as described previously to cause inner cannula 76 to reciprocate within outer cannula lumen 110 and sever tissue received in outer cannula opening 49. Fluid may be supplied via delivery sleeve 302/402 before, during, and/or after reciprocation of inner cannula 76 within outer cannula lumen 110. Severed tissue snippets and/or fluids, including but not limited to the fluids supplied via the delivery sleeve 302/402, are then aspirated through inner cannula lumen 78 and into tissue collector 58 as described previously.

In certain examples, tissue cutting device 40 may be used to cut tissues with significant quantities of vasculaturized tissues which can generate significant bleeding. One such example is a hemangioblastoma. In such cases, a hemostatic agent or sealant of the type described previously may be supplied during or after the tissue cutting procedure to minimize blood flow.

Figure 31:
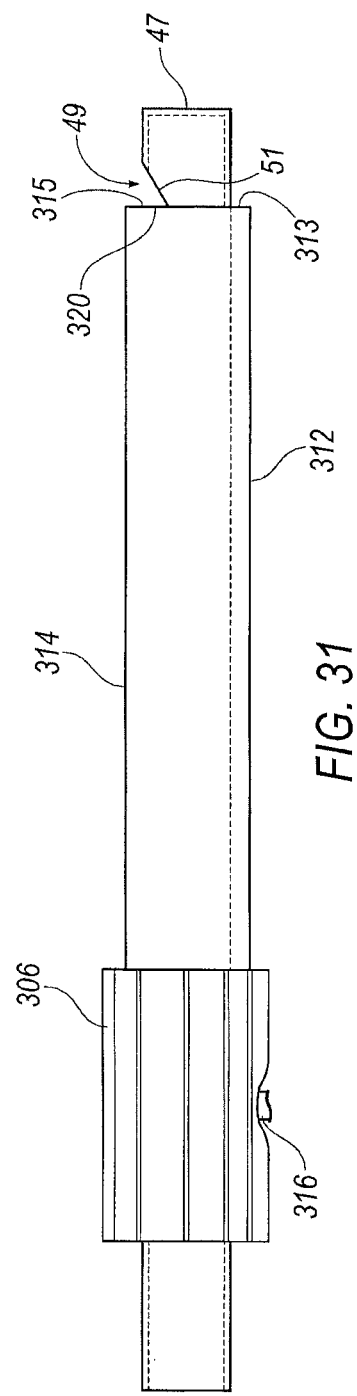
FIG. 31 is a close-up, partial side elevational view of the delivery sleeve of FIG. 1 selectively disposed along the length of the outer cannula of FIG. 1.
Figure 32:
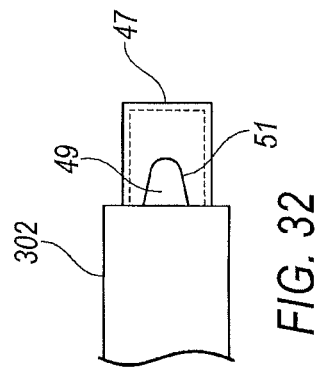
FIG. 32 is a close-up, partial top plan view of the delivery sleeve of FIG. 1 selectively disposed over a portion of the outer cannula opening of FIG. 1.

In another exemplary method, a tissue cutting system comprising tissue cutting device 40 and delivery sleeve 302 is provided, and the system is used in an aspiration mode. In accordance with the example, the surgeon selectively positions the delivery sleeve 302 along the length of outer cannula 44 to occlude a portion of outer cannula opening 49 as best seen in FIGS. 31 and 32. The delivery sleeve 302 may be used to occlude a desired percent of the open area of outer cannula opening 49 and therefore to selectively adjust the aspiration provided at outer cannula opening for a given vacuum level supplied to inner cannula lumen 78. For example, delivery sleeve 302 positions may be selected that limit the percent open area of outer cannula opening 49 to 25%, 50%, or 75% of the total area of opening 49. A vacuum level may then be supplied to inner cannula lumen 78 and may draw surrounding tissues into the partially-occluded outer cannula opening 49. In addition, fluids may be aspirated through outer cannula opening 49, inner cannula lumen 78, tissue collector 58, and collected in fluid collection canister 192 (FIG. 21A). With tissue drawn into outer cannula opening 49, motor 62 may be activated to sever the received tissue and collect it as described previously. Thus, delivery sleeve 302 effectively allows the surgeon to manually adjust the degree of aspiration at outer cannula opening 49, and correspondingly, the size of the tissue samples that are received in outer cannula opening 49 and severed by inner cannula 76. Fluid may be supplied at or near the target tissue via fluid supply channel 312 before, during, and/or after tissue resection. However, delivery sleeve 302 may also be used to adjust the degree of aspiration provided by tissue cutting device 40 without supplying fluids.

Referring now of FIGS. 41-44, an alternative embodiment of a delivery sleeve 502 will now be described. As discussed above in connection FIGS. 33 and 39, delivery sleeve 502 is selectively disposed about outer cannula 44 (i.e., the user can install or remove delivery sleeve 502 from outer cannula 44) to selectively attach an optical device (such as, for example, a fiber optic bundle) to the surgical area. Delivery sleeve 502 includes an elongated channel section similar channel section 404 described above. The elongated channel section comprises an outer cannula lumen 514 and at least one optical delivery lumen 512. Optical delivery lumen 512 is connected to the outer cannula lumen 514, at least partially, along their respective lengths. In one exemplary arrangement, optical delivery lumen 512 and outer cannula lumen 514 are arranged so as to be oriented in a co-planar manner similar to that which was shown in FIG. 34. The optical device may be selectively positioned within optical delivery lumen 512. More specifically, the optical device may be adjusted along the axial length of optical delivery lumen 512 such that it may be retracted from or extend past a distal end of optical delivery lumen 512. Further, in one exemplary arrangement, delivery sleeve 502 may be selectively rotated about outer cannula 44 such that the angular position of delivery sleeve 502 may be adjusted by the user.

Outer cannula lumen 514 is defined by a proximal end 517 (best seen in FIGS. 41 and 42). Optical delivery lumen 512 is also defined by a proximal end 519 (best seen in FIG. 42). Proximal end 519 may be slightly angled (as shown in FIG. 42), to provide ease of insertion of an optical fiber into optical delivery lumen 512. A proximal end of the delivery sleeve 502 is positioned in and supported by a hub 506. Details of the hub 506 may be seen in FIGS. 41-44, although it should be noted that for ease of explanation, only a lower section of hub 506 is illustrated. Hub 506 is defined by a body portion 503 that includes a distal face 505 and a proximal face 507. In one configuration, body portion 503 may be formed as mirror image lower and upper sections (lower section visible in FIGS. 41-44) that are configured to snap together or are otherwise connected together to form body portion 503. Body portion 503 includes a first channel 509 and a second channel 511. First channel 509 extends from distal face 505 to a first portion 507a of proximal face 507. First and second channels 509, 511 are configured to receive the proximal end of delivery sleeve 502, as best seen in FIGS. 41 and 42. In one exemplary configuration, proximal ends 517 and 519 are fixedly secured within first and second channels 509, 511 such that delivery sleeve 502 is integrally connected to body portion 506. Proximal ends 517 and 519 may be fixed to body portion 506 in any suitable member. For example, proximal ends 517 and 519 may be glued within first and second channels 509, 511.

In one embodiment, first portion 507a of proximal face 507 includes a mounting portion 510 that is configured to receive distal end face 59 of upper housing 52 of tissue cutting device 40. A mounting flange 521 may also be provided for receiving a mounting ring 422 (as shown in FIG. 39, for example) disposed about a portion of upper housing 52. Further, body portion 503 may also include a proximally extending clip member 523. As may be seen in FIG. 33, clip member 523 is configured to extend around and grasp a portion of mounting ring 422 to provide a quick connect/release mechanism to secure hub 506 to tissue cutting device 40. However, it is understood that other mechanisms for selective attachment of hub 506 to tissue cutting device 40 are also contemplated.

In one embodiment, second portion 507b of proximal face 507 may be configured with a connecting portion 525 that is in communication with second channel 511. In one exemplary arrangement connecting portion 525 comprises a distal portion 527 and a proximal portion 529. Second channel 511 opens into distal portion 527, while proximal portion 529 opens into second portion 507b of proximal face 507. In one configuration, connection portion 525 is configured with an annular retaining lip 531 that extends at least partially between distal and proximal portions 527, 529. In yet another exemplary configuration, annular retaining lip 531 extends continuously around the inner surface of connecting portion 525. In one exemplary arrangement, connecting portion 525 is configured to be funnel shaped such that connecting portion 525 is self-directing to deliver optical fibers, or the like, thereby providing ease of insertion. Optical fibers or a probe member may be selectively mounted to the connecting portion 525. Alternatively, optical fibers or a probe member may be pre-assembled with hub 503.

Body portion 506 may also be provided with retaining fingers 533. As seen in FIG. 33, when hub 503 is installed on tissue cutting device 40, retaining fingers 533 are disposed on either above or below a portion of tissue cutting device 40, along each side of tissue cutting device 40. When installed, fingers 533 serve to frictionally engage either tissue cutting device 40 or, if provided, mounting ring 422 so as to rotationally fix hub 503 with tissue cutting device 40. In other words, fingers 533 prevent hub 503 from rotating.

Optical delivery lumen 512 allows for effectively coupling tissue cutting device 40 to another separate device to provide integrated visualization and to assist in differentiation of critical structures, healthy tissue and diseased tissue. More specifically, optical delivery lumen 512 is coupled with another separate device to deliver, for example, a fiber optic bundle for the transmission and reception of reflected light to a remote sensor, filtered light to illuminate interaction of dye with tissue or an ultrasound probe or other devices.

In one exemplary embodiment, a fiber optic bundle may be positioned within second channel 511 and delivered into the optical delivery lumen 512 of the delivery sleeve 502. In one exemplary arrangement, the fiber optic bundle may be used for photocoagulation of blood. More specifically, the fiber optic is used as a laser to produce light in a suitable wavelength that may be selectively absorbed by hemoglobin, to coagulate blood or ablate blood vessels.

In another exemplary embodiment, the fiber optic bundle may be used in connection with a tissue-soldering technique to repair a dural defect. In this configuration, the fiber optic bundle may be used to deliver laser light to weld a substrate directly with a tissue covering (either natural or synthetic) or with the use of a soldering fluid, both of which creates a water-tight seal and provides for more effective healing. Indeed, the tissue-soldering technique may be used to create a water-tight seal to retain cerebrospinal fluid within the dura. In another embodiment, the tissue-soldering technique may be employed to weld a tissue vessel (i.e., a natural channel within the body that communicates tissue or fluid) so as to preserve functionality of the vessel or vessel patency.

In yet another exemplary embodiment, the fiber optic bundle may be delivered through the delivery sleeve 402 to deliver certain wavelengths of light for various applications in connection with the tissue cutting device 40. For example, the fiber optic bundle may be utilized for photodynamic therapy. More specifically, in one embodiment, first a predetermined chemical composition (i.e., a dye) is delivered to the target tissue. To activate the chemical composition, a predetermined wavelength of light is delivered by the fiber optic bundle through optical delivery lumen 412. The activation of the chemical composition can perform a number of desired results. For example, in one exemplary arrangement, the predetermined chemical composition selected bonds to proteins from diseased cells. Accordingly, specific wavelengths or colors of light are delivered by the fiber optic bundle, thereby illuminating the diseased tissue (by virtue of the bonding between the chemical composition and the proteins). With this illumination, tissue cutting device 40 may be more efficiently and safely used to resect diseased or abnormal tissue. In other embodiments, the predetermined chemical composition may be used in connection with selected wavelengths of light to activate a therapeutic reaction.

In another exemplary embodiment, delivery sleeve 402 may used with spectroscopy. More specifically, light may be delivered through the optical lumen 412 and reflected proximally from the surgical field or the area of interest. The fiber optic bundle or light probe is operatively connected to a console such that the reflected light is delivered to the console. A sensor in the console (i.e., the sensor is remotely located from the point of detection receives the reflected light to trigger a signal to the user based on predetermined parameters. In other words, the natural florescence of the tissue is then reflected back to the console to inform the user whether or not the tissue is diseased or healthy. Because the delivery sleeve 402 is operatively connected to the tissue cutting device 40, use of the spectroscopy permits the user to obtain information about the tissue adjacent to the cutting element such that diseased tissue may be excised more quickly and effectively and healthy tissue is preserved.

Similarly, in yet another exemplary embodiment, the use of optical coherence tomography ("OCT") may be used. More specifically, a fiber optic bundle may be operatively connected to a console that employs a low-coherence-interfermoetry to produce a two-dimensional image from tissue structures. Because the delivery sleeve 402 is operatively connected to the tissue cutting device 40, use of OCT permits the user to obtain information about the tissue adjacent to the cutting element such that diseased tissue may be excised more quickly and effectively and healthy tissue is preserved.

In yet another exemplary arrangement, an intravascular ultrasound device may be delivered through delivery sleeve 402 (and more specifically, optical lumen 412). The ultrasound device is configured to permit viewing of vessels that are positioned so as to be adjacent to the structure that is being resected or (those imbedded therein). The ultrasound device provides visualization of blood flow in a region of interest and acts as a doppler to determine tissue characteristics. For example, in one instance, the ultrasound device may be used to determine if there is fluid running through nearby vessels that are not necessarily visible. In such a configuration, sound is beamed into an area of interest. The sound reflects off of a moving target, such as blood passing through a vessel, and the pitch of the sound wave changes may change in accordance with the Doppler Effect. The ultrasound device can be configured to detect subtle pitch changes and record them visually, creating an image showing where blood is flowing. The ultrasound device may, for example, be used to map out the location of critical structures adjacent suspected tumors, thereby providing a physician the ability to evaluate treatment options and to avoid damaging such structures when tissue cutting device 40 is being utilized.

While described in the context of an intravascular ultrasound device, it is also understood a non-ultrasonic/imaging Doppler probe may also be used as described above. More specifically, a Doppler probe that utilizes an amplifier operatively attached to a microphone to audibly indicate blood flow may be provided. In one exemplary configuration, the probe emits an audible pulsed signal, which varies when the probe is placed upon (or near) a vessel within which is there is flow. The frequency (i.e., pitch) of the signal is proportional to the blood velocity within the vessel. Accordingly, as set forth in the description above, positioning of the Doppler probe through the delivery sleeve 402 assists in identifying and accessing critical blood vessels and other structures, adjacent the tissue cutting device 40.

In another instance, the ultrasound may be used to view extent of a tumor for resection. In yet another instance, the ultrasound device may also be used within the delivery sleeve 402 (with the tissue cutting device 40) for providing visualization beyond a tumor to assist the user in ascertaining the fibrotic nature of the tissue, thereby distinguishing between healthy tissue and diseased tissue, in real-time and in conjunction with resection. In other words, the ultrasound device may be provided with tissue characteristic interpretation, (i.e., elastography). This configuration provides for parallel insertion and utilization of both an ultrasound device and tissue cutting device 40, thereby minimizing multiple introduction and removal operations rather than prior art systems which required serial insertion and removal, thereby extending the procedure and potential loss of focus for the surgeon. Moreover, use of an ultrasound probe through delivery sleeve 402 in connection with a tissue cutting device 40 is especially advantageous in minimally invasive neurosurgical procedures in that space is very limited. Accordingly, traditional large bore ultrasound probes are undesirable.

In another exemplary embodiment a monopolar or bipolar device/probe may be used in conjunction with and placed down the delivery sleeve 402 to assist in the coagulation of blood at the surgical site. The monopolar or bipolar device/probe may be attached to a cautery generator and thereby provide the user with simultaneous tissue cutting and blood coagulation of severed blood vessels.

It will be appreciated that the tissue cutting devices and methods described herein have broad applications. The foregoing embodiments were chosen and described in order to illustrate principles of the methods and apparatuses as well as some practical applications. The preceding description enables others skilled in the art to utilize methods and apparatuses in various embodiments and with various modifications as are suited to the particular use contemplated. In accordance with the provisions of the patent statutes, the principles and modes of operation of this invention have been explained and illustrated in exemplary embodiments.

It is intended that the scope of the present methods and apparatuses be defined by the following claims. However, it must be understood that this invention may be practiced otherwise than is specifically explained and illustrated without departing from its spirit or scope. It should be understood by those skilled in the art that various alternatives to the embodiments described herein may be employed in practicing the claims without departing from the spirit and scope as defined in the following claims. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. Furthermore, all terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary. It is intended that the following claims define the scope of the invention and that the method and apparatus within the scope of these claims and their equivalents be covered thereby. In sum, it should be understood that the invention is capable of modification and variation and is limited only by the following claims.

What is claimed as new and desired to be protected by Letters Patent of the United States is:

1. A tissue removal system, comprising:
   a handpiece;
   an outer cannula having an outer cannula lumen, a proximal end, a distal end, and an outer cannula opening at the distal end, wherein the opening defines a cutting edge for severing tissue;
   and
   a delivery sleeve disposed about the outer cannula, wherein the delivery sleeve comprises an outer cannula channel and at least one delivery channel extending the length of the delivery sleeve, the delivery sleeve being removable from the outer cannula at the distal end of the outer cannula.

2. The tissue removal system of claim 1, wherein when the delivery sleeve is in an uninstalled condition, the at least one delivery channel is separated from the outer cannula channel along the length of the delivery sleeve.

3. The tissue removal system of claim 1, wherein the outer cannula is rotatable with respect to the delivery sleeve and the handpiece.

4. The tissue removal system of claim 1, wherein the delivery sleeve is at least partially constructed of an imageable material.

5. The tissue removal system of claim 1, wherein at least a portion of the delivery sleeve is visible under positron emission tomography.

6. The tissue removal system of claim 1, further comprising a source of irrigant in fluid communication with the at least one delivery channel.

7. The tissue removal system of claim 1, further comprising a source of a hemostatic agent in communication with the at least one delivery channel.

8. The tissue removal system of claim 1, further comprising a source of a tissue sealing agent in fluid communication with the at least one delivery channel.

9. The tissue removal system of claim 1, further comprising an optical device positioned in the at least one delivery channel.

10. The tissue removal system of claim 9, wherein the optical device is one of a fiber optic bundle and an ultrasound probe.

11. The tissue removal system of claim 1, further comprising a hub which includes a first channel and a second channel each disposed within the hub, wherein the outer cannula channel and the delivery channel being in communication with the first and second channel, respectively.

12. The tissue removal system of claim 11, wherein the second channel is defined by distal and proximal openings, and where in the proximal opening is configured to be positioned adjacent a portion of a tissue cutting device when the hub is connected to the tissue cutting device.

13. The tissue removal system of claim 12, wherein the proximal opening of the second channel further comprises a connecting portion.

14. The tissue removal system of claim 13, wherein the connecting portion is configured to receive a valve member to fluidly connect the delivery channel to a fluid supply source.

15. The tissue removal system of claim 14, wherein the valve member is selectively connected to the connecting portion.

16. The tissue removal system of claim 14, wherein the connecting portion is configured to receive one of an optical device and probe member.

17. The tissue removal system of claim 12, wherein the first channel is defined by distal and proximal openings, and wherein the proximal opening is configured to selectively mate with a portion of the tissue cutting device.

18. The tissue removal system of claim 12, wherein the hub further includes a retaining member that may selectively connect to a portion of the tissue cutting device so as to fixedly secure the hub to the tissue cutting device in a rotationally fixed manner.

19. A tissue removal system, comprising:

a handpiece;

an outer cannula having an outer cannula lumen, a proximal end, a distal end, and an outer cannula opening at the distal end, wherein the opening defines a cutting edge for severing tissue; and a delivery sleeve insertable at the distal end of the outer cannula and arranged around the outer cannula and forming an outer cannula channel and at least one delivery channel when the delivery sleeve is in an installed condition, wherein the delivery channel extends the length of the delivery sleeve.

20. A tissue removal system, comprising:

a handpiece;

an outer cannula having an outer cannula lumen, a proximal end, a distal end, and an outer cannula opening at the distal end, wherein the opening defines a cutting edge for severing tissue;

a delivery sleeve disposed about the outer cannula, wherein the delivery sleeve comprises an outer cannula channel and at least one delivery channel extending the length of the delivery sleeve, the delivery sleeve being removable from the outer cannula at the distal end of the outer cannula; and a hub which includes a first channel and a second channel each disposed within the hub, wherein the outer cannula channel and the delivery channel being in communication with the first and second channel, respectively.

* * * * *